(12) United States Patent
LaVon et al.

(10) Patent No.: US 7,737,324 B2
(45) Date of Patent: Jun. 15, 2010

(54) DISPOSABLE ABSORBENT ARTICLE HAVING DEPLOYABLE CHASSIS EARS

(75) Inventors: Gary Dean LaVon, Liberty Township, OH (US); Michael Patrick Hayden, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 128 days.

(21) Appl. No.: 11/286,934

(22) Filed: Nov. 23, 2005

(65) Prior Publication Data

US 2007/0118091 A1    May 24, 2007

(51) Int. Cl.
*A61F 13/15* (2006.01)
*A61F 13/20* (2006.01)

(52) U.S. Cl. ...................... 604/367; 604/380

(58) Field of Classification Search ............ 604/385.01, 604/385.03, 385.24–385.27, 386–399
See application file for complete search history.

(56) References Cited

U.S. PATENT DOCUMENTS

| | | |
|---|---|---|
| 1,733,997 A | 10/1929 | Marr |
| 1,734,499 A | 11/1929 | Marinsky |
| 1,989,283 A | 1/1935 | Limacher |
| 2,058,509 A | 10/1936 | Rose |
| 2,271,676 A | 2/1942 | Bjornbak |
| 2,450,789 A | 10/1948 | Frieman |
| 2,508,811 A | 5/1950 | Best et al. |
| 2,568,910 A | 9/1951 | Condylis |
| 2,570,796 A | 10/1951 | Gross |
| 2,570,963 A | 10/1951 | Mesmer |
| 2,583,553 A | 1/1952 | Faure |
| 2,705,957 A | 4/1955 | Mauro |
| 2,788,786 A | 4/1957 | Dexter |
| 2,798,489 A | 7/1957 | Behrman |
| 2,807,263 A | 9/1957 | Newton |
| 2,830,589 A | 4/1958 | Doner |
| 2,890,700 A | 6/1959 | Lönberg-Holm |

(Continued)

FOREIGN PATENT DOCUMENTS

DE    1973 2499 A1    2/1999

(Continued)

OTHER PUBLICATIONS

U.S. Appl. No. 11/133,818, filed May 20, 2005, LaVon et al.

(Continued)

*Primary Examiner*—Michele Kidwell
(74) *Attorney, Agent, or Firm*—Richard L. Alexander

(57) ABSTRACT

A simple disposable absorbent article including a chassis and an absorbent assembly. The chassis includes laterally opposing side flaps formed by laterally inwardly folded portions of the chassis and deployable chassis ears formed by other laterally inwardly folded portions of the chassis. Each chassis ear is held laterally inwardly folded until being deployed by being released and unfolded laterally outward so as to project laterally outward beyond the adjacent side flap. Fastening elements may be disposed on at least two of the chassis ears, the fastening elements being adapted for fastening the front waist region to the back waist region to encircle a waist and legs of a wearer. The chassis may be extensible. The absorbent assembly may be attached in a cruciform pattern to the chassis to allow portions of the chassis underlying the absorbent assembly and lying outside the cruciform attachment pattern to extend laterally.

15 Claims, 15 Drawing Sheets

U.S. PATENT DOCUMENTS

| | | |
|---|---|---|
| 2,890,701 A | 6/1959 | Weinman |
| 2,898,912 A | 8/1959 | Adams |
| 2,931,361 A | 4/1960 | Sostsrin |
| 2,977,957 A | 4/1961 | Clyne |
| 3,207,158 A | 9/1965 | Yoshitake et al. |
| 3,386,442 A | 6/1968 | Sabee |
| 3,561,446 A | 2/1971 | Jones |
| 3,572,342 A | 3/1971 | Lindquist et al. |
| 3,572,432 A | 3/1971 | Burton |
| 3,578,155 A | 5/1971 | Small et al. |
| 3,592,194 A | 7/1971 | Duncan |
| 3,610,244 A | 10/1971 | Jones |
| 3,618,608 A | 11/1971 | Brink |
| 3,642,001 A | 2/1972 | Sabee |
| 3,653,381 A | 4/1972 | Warnken |
| 3,688,767 A | 9/1972 | Goldstein |
| 3,710,797 A | 1/1973 | Marsan |
| 3,731,688 A | 5/1973 | Litt et al |
| 3,756,878 A | 9/1973 | Willot |
| 3,774,241 A | 11/1973 | Zerkle |
| 3,776,233 A | 12/1973 | Schaar |
| 3,814,100 A | 6/1974 | Nystrand et al. |
| 3,828,784 A | 8/1974 | Zoephel |
| 3,840,418 A | 10/1974 | Sabee |
| 3,847,702 A | 11/1974 | Jones |
| 3,848,595 A | 11/1974 | Endres |
| 3,848,597 A | 11/1974 | Endres |
| 3,860,003 A | 1/1975 | Buell |
| 3,863,637 A | 2/1975 | MacDonald et al. |
| 3,882,870 A | 5/1975 | Hathaway |
| 3,884,234 A | 5/1975 | Taylor |
| 3,900,032 A | 8/1975 | Heurlen |
| 3,920,017 A | 11/1975 | Karami |
| 3,924,626 A | 12/1975 | Lee et al. |
| 3,926,189 A | 12/1975 | Taylor |
| 3,929,134 A | 12/1975 | Karami |
| 3,929,135 A | 12/1975 | Thompson |
| 3,930,501 A | 1/1976 | Schaar |
| 3,938,523 A | 2/1976 | Gilliland et al. |
| 3,968,799 A | 7/1976 | Schrading |
| 3,978,861 A | 9/1976 | Schaar |
| 3,981,306 A | 9/1976 | Krusko |
| 3,987,794 A | 10/1976 | Schaar |
| 3,995,637 A | 12/1976 | Schaar |
| 3,995,640 A | 12/1976 | Schaar |
| 3,999,547 A | 12/1976 | Hernandez |
| 4,014,338 A | 3/1977 | Schaar |
| 4,034,760 A | 7/1977 | Amirsakis |
| 4,074,508 A | 2/1978 | Reid |
| 4,084,592 A | 4/1978 | Tritsch |
| 4,100,922 A | 7/1978 | Hernandez |
| 4,257,418 A | 3/1981 | Hessner |
| 4,296,750 A | 10/1981 | Woon et al. |
| 4,315,508 A | 2/1982 | Bolick |
| 4,324,246 A | 4/1982 | Mullane et al. |
| 4,342,314 A | 8/1982 | Radel et al. |
| 4,388,075 A | 6/1983 | Mesek et al. |
| 4,461,621 A | 7/1984 | Karami et al. |
| 4,463,045 A | 7/1984 | Ahr et al. |
| 4,475,912 A | 10/1984 | Coates |
| 4,490,148 A | 12/1984 | Beckeström |
| 4,527,990 A | 7/1985 | Sigl |
| 4,578,072 A | 3/1986 | Lancaster |
| 4,578,702 A | 3/1986 | Campbell |
| 4,585,450 A | 4/1986 | Rosch et al. |
| 4,589,878 A | 5/1986 | Mitrani |
| 4,601,717 A | 7/1986 | Blevins |
| 4,606,964 A | 8/1986 | Wideman |
| 4,610,678 A | 9/1986 | Weisman et al. |
| 4,623,342 A | 11/1986 | Ito et al. |
| 4,636,207 A | 1/1987 | Buell |
| 4,641,381 A | 2/1987 | Heran et al. |
| 4,670,011 A | 6/1987 | Mesek |
| 4,670,012 A | 6/1987 | Johnson |
| 4,680,030 A | 7/1987 | Coates et al. |
| 4,681,581 A | 7/1987 | Coates |
| 4,690,463 A | 9/1987 | Hart |
| 4,690,680 A | 9/1987 | Higgins |
| 4,695,278 A | 9/1987 | Lawson |
| 4,704,115 A | 11/1987 | Buell |
| 4,704,116 A | 11/1987 | Enloe |
| 4,731,066 A | 3/1988 | Korpman |
| 4,747,846 A | 5/1988 | Boland et al. |
| 4,781,711 A | 11/1988 | Houghton et al. |
| 4,787,896 A | 11/1988 | Houghton et al. |
| 4,795,454 A | 1/1989 | Dragoo |
| 4,802,884 A | 2/1989 | Fröidh et al. |
| 4,808,176 A | 2/1989 | Kielpikowski |
| 4,834,735 A | 5/1989 | Alemany et al. |
| 4,834,740 A | 5/1989 | Suzuki et al. |
| 4,834,742 A | 5/1989 | Wilson et al. |
| 4,838,886 A | 6/1989 | Kent |
| 4,846,825 A | 7/1989 | Enloe et al. |
| 4,861,652 A | 8/1989 | Lippert et al. |
| 4,888,231 A | 12/1989 | Angstadt |
| 4,892,528 A | 1/1990 | Suzuki et al. |
| 4,892,536 A | 1/1990 | DesMarais et al. |
| 4,900,317 A | 2/1990 | Buell |
| 4,904,251 A | 2/1990 | Igaue et al. |
| 4,909,802 A | 3/1990 | Ahr et al. |
| 4,909,803 A | 3/1990 | Aziz et al. |
| 4,940,463 A | 7/1990 | Leathers et al. |
| 4,940,464 A | 7/1990 | Van Gompel et al. |
| 4,950,264 A | 8/1990 | Osborn |
| 4,963,140 A | 10/1990 | Robertson et al. |
| 4,968,313 A | 11/1990 | Sabee |
| 4,990,147 A | 2/1991 | Freeland |
| 5,006,394 A | 4/1991 | Baird |
| 5,019,072 A | 5/1991 | Polski |
| 5,021,051 A | 6/1991 | Hiuke |
| 5,032,120 A | 7/1991 | Freeland et al. |
| 5,034,008 A | 7/1991 | Breitkopf |
| 5,037,416 A | 8/1991 | Allen et al. |
| 5,071,414 A | 12/1991 | Elliott |
| 5,085,654 A | 2/1992 | Buell |
| 5,092,861 A | 3/1992 | Nomura et al. |
| 5,114,420 A | 5/1992 | Igaue et al. |
| 5,135,522 A | 8/1992 | Fahrenkrug et al. |
| D329,697 S | 9/1992 | Fahrenkrug et al. |
| 5,151,092 A | 9/1992 | Buell et al. |
| 5,190,606 A | 3/1993 | Merkatoris et al. |
| 5,204,997 A | 4/1993 | Suzuki et al. |
| 5,221,274 A | 6/1993 | Buell et al. |
| 5,235,515 A | 8/1993 | Ungpiyakul et al. |
| 5,246,431 A | 9/1993 | Minetola et al. |
| 5,246,432 A | 9/1993 | Suzuki et al. |
| 5,246,433 A | 9/1993 | Hasse et al. |
| 5,260,345 A | 11/1993 | Desmarais et al. |
| 5,269,775 A | 12/1993 | Freeland et al. |
| 5,312,386 A | 5/1994 | Correa et al. |
| 5,358,500 A | 10/1994 | LaVon et al. |
| 5,366,782 A | 11/1994 | Curro et al. |
| 5,387,209 A | 2/1995 | Yamamoto et al. |
| 5,397,316 A | 3/1995 | LaVon et al. |
| H1440 H | 5/1995 | New et al. |
| 5,415,644 A | 5/1995 | Enloe |
| 5,476,458 A | 12/1995 | Glaug et al. |
| 5,518,801 A | 5/1996 | Chappell et al. |
| 5,531,730 A | 7/1996 | Dreier |
| 5,542,943 A | 8/1996 | Sageser |
| 5,549,592 A | 8/1996 | Fries et al. |
| 5,549,593 A | 8/1996 | Ygge et al. |
| 5,554,145 A | 9/1996 | Roe et al. |
| 5,569,234 A | 10/1996 | Buell et al. |

| | | | | | | |
|---|---|---|---|---|---|---|
| 5,571,096 | A | 11/1996 | Dobrin et al. | 6,334,858 B1 | 1/2002 | Rönnberg et al. |
| 5,580,411 | A | 12/1996 | Nease et al. | 6,336,922 B1 | 1/2002 | VanGompel et al. |
| 5,584,829 | A | 12/1996 | Lavash et al. | 6,350,332 B1 | 2/2002 | Thomas et al. |
| 5,607,416 | A | 3/1997 | Yamamoto et al. | 6,364,863 B1 | 4/2002 | Yamamoto et al. |
| 5,607,537 | A | 3/1997 | Johnson et al. | 6,402,729 B1 | 6/2002 | Boberg et al. |
| 5,607,760 | A | 3/1997 | Roe | 6,402,731 B1 | 6/2002 | Suprise et al. |
| 5,609,587 | A | 3/1997 | Roe | 6,410,820 B1 | 6/2002 | Mcfall et al. |
| 5,613,959 | A | 3/1997 | Roessler et al. | 6,413,249 B1 | 7/2002 | Turi et al. |
| 5,622,589 | A | 4/1997 | Johnson et al. | 6,419,667 B1 | 7/2002 | Avalon et al. |
| 5,624,424 | A | 4/1997 | Saisaka et al. | 6,423,048 B1 | 7/2002 | Suzuki et al. |
| 5,625,222 | A | 4/1997 | Yoneda et al. | 6,432,098 B1 | 8/2002 | Kline et al. |
| 5,626,571 | A | 5/1997 | Young et al. | 6,432,099 B2 | 8/2002 | Rönnberg |
| 5,635,191 | A | 6/1997 | Roe et al. | 6,443,933 B1 | 9/2002 | Suzuki et al. |
| 5,643,243 | A | 7/1997 | Klemp | 6,461,342 B2 | 10/2002 | Tanji et al. |
| 5,643,588 | A | 7/1997 | Roe et al. | 6,461,343 B1 | 10/2002 | Schaefer et al. |
| H1674 | H | 8/1997 | Ames et al. | 6,475,201 B2 | 11/2002 | Saito et al. |
| 5,662,638 | A | 9/1997 | Johnson et al. | 6,494,872 B1 | 12/2002 | Suzuki et al. |
| 5,674,215 | A | 10/1997 | Ronnberg | 6,494,873 B2 | 12/2002 | Karlsson et al. |
| 5,685,874 | A | 11/1997 | Buell et al. | 6,520,947 B1 | 2/2003 | Tilly et al. |
| 5,691,035 | A | 11/1997 | Chappell et al. | 6,524,294 B1 | 2/2003 | Hilston et al. |
| 5,691,036 | A | 11/1997 | Lin et al. | 6,547,774 B2 | 4/2003 | Ono et al. |
| 5,723,087 | A | 3/1998 | Chappell et al. | 6,570,056 B1 | 5/2003 | Tanzer et al. |
| 5,749,866 | A | 5/1998 | Roe et al. | 6,572,601 B2 | 6/2003 | Suprise et al. |
| 5,752,947 | A | 5/1998 | Awolin | 6,572,602 B2 | 6/2003 | Furuya et al. |
| 5,772,825 | A | 6/1998 | Schmitz | 6,574,602 B1 | 6/2003 | Absar et al. |
| 5,776,121 | A | 7/1998 | Roe et al. | 6,579,275 B1 | 6/2003 | Pozniak et al. |
| 5,779,831 | A | 7/1998 | Schmitz | 6,585,713 B1 | 7/2003 | LeMahieu et al. |
| 5,797,894 | A | 8/1998 | Cadieux et al. | 6,602,234 B2 | 8/2003 | Klemp et al. |
| 5,810,800 | A | 9/1998 | Hunter et al. | 6,605,070 B2 | 8/2003 | Ludwig et al. |
| 5,814,035 | A | 9/1998 | Gryskiewicz et al. | 6,626,881 B2 | 9/2003 | Shingu et al. |
| 5,820,618 | A | 10/1998 | Roberts et al. | 6,648,869 B1 | 11/2003 | Gillies et al. |
| 5,846,232 | A | 12/1998 | Serbiak et al. | 6,648,870 B2 | 11/2003 | Itoh et al. |
| 5,851,204 | A | 12/1998 | Mizutani | 6,648,871 B2 | 11/2003 | Kusibojoska et al. |
| 5,853,402 | A | 12/1998 | Faulks et al. | 6,682,515 B1 | 1/2004 | Mizutani et al. |
| 5,865,823 | A | 2/1999 | Curro | 6,682,596 B2 | 1/2004 | Zehnder et al. |
| 5,873,868 | A | 2/1999 | Nakahata | 6,689,115 B1 | 2/2004 | Popp et al. |
| 5,876,391 | A | 3/1999 | Roe et al. | 6,706,028 B2 | 3/2004 | Roe et al. |
| 5,891,544 | A | 4/1999 | Chappell et al. | 6,726,792 B1 | 4/2004 | Johnson et al. |
| 5,897,545 | A | 4/1999 | Kline et al. | 6,730,070 B2 | 5/2004 | Holmquist |
| 5,904,673 | A | 5/1999 | Roe et al. | 6,755,808 B2 | 6/2004 | Balogh et al. |
| 5,931,825 | A | 8/1999 | Kuen et al. | 6,818,083 B2 | 11/2004 | Mcamish et al. |
| 5,947,949 | A | 9/1999 | Inoue et al. | 6,840,930 B1 | 1/2005 | Miyamoto et al. |
| 5,951,536 | A | 9/1999 | Osborn, III et al. | 6,880,211 B2 | 4/2005 | Jackson et al. |
| 5,957,908 | A | 9/1999 | Kline et al. | 6,923,797 B2 | 8/2005 | Shinohara et al. |
| 5,968,029 | A | 10/1999 | Chappell et al. | 6,962,578 B1 | 11/2005 | LaVon |
| 6,004,306 | A | 12/1999 | Robles et al. | 6,972,010 B2 | 12/2005 | Pesce et al. |
| 6,022,430 | A | 2/2000 | Blenke et al. | 7,013,941 B2 | 3/2006 | Schneider et al. |
| 6,022,431 | A | 2/2000 | Blenke et al. | 7,014,632 B2 | 3/2006 | Takino et al. |
| 6,042,673 | A | 3/2000 | Johnson et al. | 7,014,649 B2 | 3/2006 | Bacher |
| 6,102,892 | A | 8/2000 | Putzer et al. | 7,037,299 B2 | 5/2006 | Turi et al. |
| 6,107,537 | A | 8/2000 | Elder et al. | 7,048,726 B2 | 5/2006 | Kusagawa et al. |
| 6,110,157 | A | 8/2000 | Schmidt | 7,066,921 B2 | 6/2006 | Schmoker et al. |
| 6,117,121 | A | 9/2000 | Faulks et al. | D525,706 S | 7/2006 | Pargass |
| 6,117,803 | A | 9/2000 | Morman et al. | 7,112,193 B2 | 9/2006 | Otsubo |
| 6,120,486 | A | 9/2000 | Toyoda et al. | 7,160,281 B2 | 1/2007 | Leminh et al. |
| 6,120,487 | A | 9/2000 | Ashton | 7,195,622 B2 | 3/2007 | Lindstrom |
| 6,120,489 | A | 9/2000 | Johnson et al. | 7,211,072 B2 | 5/2007 | Nawata et |
| 6,120,866 | A | 9/2000 | Arakawa et al. | 7,220,251 B2 | 5/2007 | Otsubo et al. |
| 6,129,720 | A | 10/2000 | Blenke et al. | 7,288,079 B2 | 10/2007 | Toyoshima et al |
| 6,156,023 | A | 12/2000 | Yoshioka | 7,291,137 B2 | 11/2007 | LaVon et al. |
| 6,156,424 | A | 12/2000 | Taylor | 7,314,465 B2 | 1/2008 | Van Gompel et al. |
| 6,165,160 | A | 12/2000 | Suzuki et al. | 7,318,820 B2 | 1/2008 | Lavon et al. |
| 6,174,302 | B1 | 1/2001 | Kumasaka | 7,320,684 B2 | 1/2008 | LaVon et al. |
| 6,177,607 | B1 | 1/2001 | Blaney et al. | 7,347,848 B2 | 3/2008 | Fernfors |
| 6,186,996 | B1 | 2/2001 | Martin | 7,435,244 B2 | 10/2008 | Schroer, Jr. et al. |
| 6,210,390 | B1 | 4/2001 | Karlsson | 2002/0045881 A1 | 4/2002 | Kusibojoska et al. |
| 6,238,380 | B1 | 5/2001 | Sasaki | 2002/0087139 A1 | 7/2002 | Popp et al. |
| 6,241,716 | B1 | 6/2001 | Rönnberg | 2002/0099351 A1 | 7/2002 | Onishi et al. |
| 6,254,294 | B1 | 7/2001 | Muhar | 2002/0138063 A1 | 9/2002 | Kuen et al. |
| 6,306,122 | B1 | 10/2001 | Narawa et al. | 2002/0151861 A1 | 10/2002 | Klemp et al. |
| 6,312,420 | B1 | 11/2001 | Sasaki et al. | 2002/0173767 A1 | 11/2002 | Popp et al. |
| 6,322,552 | B1 | 11/2001 | Blenke et al. | 2003/0003269 A1 | 1/2003 | Lee et al. |
| 6,325,787 | B1 | 12/2001 | Roe et al. | 2003/0088223 A1 | 5/2003 | Vogt et al. |

| | | |
|---|---|---|
| 2003/0088230 A1 | 5/2003 | Balogh et al. |
| 2003/0105447 A1 | 6/2003 | Widlund et al. |
| 2003/0144644 A1 | 7/2003 | Murai et al. |
| 2003/0148694 A1 | 8/2003 | Ghiam |
| 2003/0233082 A1 | 12/2003 | Kline et al. |
| 2004/0022998 A1 | 2/2004 | Miyamoto et al. |
| 2004/0082928 A1 | 4/2004 | Pesce et al. |
| 2004/0122411 A1 | 6/2004 | Hancock-Cooke |
| 2004/0127868 A1 | 7/2004 | Olson et al. |
| 2004/0147890 A1 | 7/2004 | Nakahata et al. |
| 2004/0162536 A1 | 8/2004 | Becker et al. |
| 2004/0167486 A1 | 8/2004 | Busam et al. |
| 2004/0225271 A1 | 11/2004 | Datta et al. |
| 2004/0236299 A1 | 11/2004 | Tsang et al. |
| 2004/0236304 A1 | 11/2004 | Coates et al. |
| 2004/0249355 A1 | 12/2004 | Tanio et al. |
| 2005/0004548 A1 | 1/2005 | Otsubo et al. |
| 2005/0038401 A1 | 2/2005 | Suzuki et al. |
| 2005/0085784 A1 | 4/2005 | LeMinh et al. |
| 2005/0131373 A1 | 6/2005 | Wright et al. |
| 2005/0171499 A1 | 8/2005 | Nigam et al. |
| 2005/0177126 A1 | 8/2005 | Kurata |
| 2005/0203475 A1 | 9/2005 | Lavon et al. |
| 2005/0288645 A1 | 12/2005 | LaVon |
| 2005/0288646 A1 | 12/2005 | LaVon |
| 2006/0264860 A1 | 11/2006 | Beck |
| 2006/0264861 A1 | 11/2006 | LaVon et al. |
| 2006/0271010 A1 | 11/2006 | LaVon |
| 2006/0293637 A1 | 12/2006 | LaVon et al. |
| 2006/0293638 A1 | 12/2006 | LaVon et al. |
| 2007/0032770 A1 | 2/2007 | LaVon et al. |
| 2007/0034348 A1 | 2/2007 | Aoyama et al. |
| 2007/0049897 A1 | 3/2007 | Lavon et al. |
| 2007/0066951 A1 | 3/2007 | Lavon et al. |
| 2007/0066952 A1 | 3/2007 | Lavon et al. |
| 2007/0066953 A1 * | 3/2007 | LaVon et al. ............... 604/392 |
| 2007/0118088 A1 | 5/2007 | LaVon |
| 2007/0118089 A1 | 5/2007 | LaVon |
| 2007/0144660 A1 | 6/2007 | O'Sickey et al. |
| 2007/0173780 A1 | 7/2007 | LaVon |
| 2007/0173782 A1 | 7/2007 | LaVon et al. |
| 2008/0183149 A1 | 7/2008 | LaVon et al. |
| 2008/0208155 A1 | 8/2008 | LaVon et al. |
| 2008/0208156 A1 | 8/2008 | LaVon et al. |
| 2008/0234649 A1 | 9/2008 | Hamall et al. |

FOREIGN PATENT DOCUMENTS

| | | |
|---|---|---|
| DE | 19732499 | 2/1999 |
| EP | 0 206 208 A1 | 12/1986 |
| EP | 374542 | 6/1990 |
| EP | 0 403 832 A1 | 12/1990 |
| EP | 0403832 | 12/1990 |
| EP | 374542 B1 | 11/1994 |
| EP | 0 761 194 A2 | 3/1997 |
| EP | 0 893 115 A2 | 1/1999 |
| EP | 0 916 327 A1 | 5/1999 |
| EP | 0 951 890 A2 | 10/1999 |
| EP | 0 793 469 B9 | 6/2002 |
| EP | 1 224 922 A2 | 7/2002 |
| EP | 1 447 066 A1 | 8/2004 |
| EP | 1 447 067 A1 | 8/2004 |
| ES | 2 213 491 A1 | 8/2004 |
| FR | 2 566 631 A1 | 1/1986 |
| FR | 2 612 770 A1 | 9/1988 |
| FR | 2 810 234 A1 | 12/2001 |
| GB | 1 307 441 | 2/1973 |
| GB | 1 513 055 | 6/1978 |
| GB | 2 101 468 A | 1/1983 |
| GB | 2 262 873 A | 7/1993 |
| JP | 04 122256 A | 4/1992 |
| JP | 11318980 | 11/1999 |
| WO | WO 84/04242 A1 | 11/1984 |
| WO | WO 8404242 A1 | 11/1984 |
| WO | WO 95/16746 | 6/1995 |
| WO | WO 9516746 A1 | 6/1995 |
| WO | WO 95/19753 | 7/1995 |
| WO | WO 95/29657 A1 | 11/1995 |
| WO | WO 98/16179 A1 | 4/1998 |
| WO | WO 99/13813 A1 | 3/1999 |
| WO | WO 03/009794 A2 | 2/2003 |
| WO | WO 2004/105664 | 12/2004 |
| WO | WO 05/016211 | 2/2005 |
| WO | WO 05/081937 | 9/2005 |
| WO | WO 2005/087164 A1 | 9/2005 |
| WO | WO 2006/123976 | 11/2006 |
| WO | WO 2007/000315 A1 | 1/2007 |

OTHER PUBLICATIONS

U.S. Appl. No. 11/135,689, filed May 24, 2005, LaVon.
U.S. Appl. No. 11/140,888, filed May 31, 2005, LaVon et al.
U.S. Appl. No. 11/197,197, filed Aug. 4, 2005, LaVon et al.
U.S. Appl. No. 11/210,345, filed Aug. 24, 2005, LaVon et al.
U.S. Appl. 10/770,043, filed Feb. 2, 2004, Notice of Allowance dated Oct. 5, 2009.
U.S. Appl. 10/770,043, filed Feb. 2, 2004, Office Action dated Jun. 16, 2009.
U.S. Appl. 10/770,043, filed Feb. 2, 2004, Office Action dated Feb. 18, 2009.
U.S. Appl. No. 10/770,043, filed Feb. 2, 2004, Office Action dated Jan. 11, 2008.
U.S. Appl. No. 10/770,043, filed Feb. 2, 2004, Office Action dated Jul. 17, 2007.
U.S. Appl. No. 10/770,043, filed Feb. 2, 2004, Office Action dated Mar. 9, 2007.
U.S. Appl. No. 10/770,043, filed Feb. 2, 2004, Office Action dated Sep. 13, 2006.
U.S. Appl. No. 10/770,043, filed Feb. 2, 2004, Office Action dated Mar. 23, 2006.
U.S. Appl. No. 10/799,947, filed Mar. 10, 2005, Notice of Allowance dated Oct. 2, 2007.
U.S. Appl. No. 10/799,947, filed Mar. 10, 2005, Office Action dated Jul. 20, 2007.
U.S. Appl. No. 10/799,947, filed Mar. 10, 2005, Office Action dated Apr. 11, 2007.
U.S. Appl. No. 10/799,947, filed Mar. 10, 2005, Office Action dated Oct. 16, 2006.
U.S. Appl. No. 10/799,947, filed Mar. 10, 2005, Office Action dated Jul. 13, 2007.
U.S. Appl. No. 10/799,947, filed Mar. 10, 2005, Office Action dated Mar. 16, 2006.
U.S. Appl. No. 10/799,947, filed Mar. 10, 2005, Office Action dated Oct. 4, 2005.
U.S. Appl. No 10/880,135, filed Nov. 8, 2005, Notice of Allowance dated Jun. 17, 2005.
U.S. Appl. No 10/880,135, filed Nov. 8, 2005, Office Action dated Nov. 12, 2004.
U.S. Appl. No. 11/172,191, filed Jun. 29, 2004, Notice of Allowance dated Aug. 7, 2007.
U.S. Appl. No. 11/172,191, filed Jun. 29, 2004, Office Action dated Feb. 16, 2007.
U.S. Appl. No. 11/172,191, filed Jun. 29, 2004, Office Action dated Aug. 10, 2006.
U.S. Appl. No. 11/172,191, filed Jun. 29, 2004, Office Action dated Nov. 9, 2009.
U.S. Appl. No. 11/133,818, filed May 20, 2005, Office Action dated Apr. 1, 2009.
U.S. Appl. No. 11/133,818, filed May 20, 2005, Office Action dated Dec. 9, 2008.
U.S. Appl. No. 11/133,818, filed May 20, 2005, Office Action dated Jun. 18, 2008.
U.S. Appl. No. 11/133,818, filed May 20, 2005, Office Action dated Dec. 31, 2007.
U.S. Appl. No. 11/133,818, filed May 20, 2005, Office Action dated Jun. 26, 2007.

U.S. Appl. No. 11/135,689, filed May 31, 2005, Office Action dated Sep. 22, 2009.
U.S. Appl. No. 11/135,689, filed May 31, 2005, Office Action dated Feb. 24, 2009.
U.S. Appl. No. 11/135,689, filed May 31, 2005, Office Action dated Oct. 16, 2008.
U.S. Appl. No. 11/135,689, filed May 31, 2005, Office Action dated Apr. 3, 2008.
U.S. Appl. No. 11/135,689, filed May 31, 2005, Office Action dated Oct. 9, 2007.
U.S. Appl. No. 11/135,689, filed May 31, 2005, Office Action dated Jun. 4, 2007.
U.S. Appl. No. 11/135,689, filed May 31, 2005, Office Action dated Oct. 6, 2006.
U.S. Appl. No. 11/140,888, filed May 20, 2005, Office Action dated Dec. 17, 2009.
U.S. Appl. No. 11/140,888, filed May 20, 2005, Office Action dated Jul. 21, 2009.
U.S. Appl. No. 11/140,888, filed May 20, 2005, Office Action dated Dec. 30, 2008.
U.S. Appl. No. 11/140,888, filed May 20, 2005, Office Action dated Oct. 10, 2008.
U.S. Appl. No. 11/140,888, filed May 20, 2005, Office Action dated Mar. 28, 2008.
U.S. Appl. No. 11/140,888, filed May 20, 2005, Office Action dated Dec. 13, 2007.
U.S. Appl. No. 11/140,888, filed May 20, 2005, Office Action dated Jun. 27, 2007.
U.S. Appl. No. 11/159,916, filed Jun. 23, 2005, Notice of Allowance dated Sep. 17, 2009.
U.S. Appl. No. 11/159,916, filed Jun. 23, 2005, Notice of Allowance dated Mar. 6, 2009.
U.S. Appl. No. 11/159,916, filed Jun. 23, 2005, Office Action dated Apr. 18, 2008.
U.S. Appl. No. 11/159,916, filed Jun. 23, 2005, Office Action dated Nov. 1, 2007.
U.S. Appl. No. 11/197,197, filed Aug. 4, 2005, Office Action dated Aug. 10, 2009.
U.S. Appl. No. 11/197,197, filed Aug. 4, 2005, Office Action dated May 7, 2008.
U.S. Appl. No. 11/197,197, filed Aug. 4, 2005, Office Action dated Nov. 7, 2007.
U.S. Appl. No. 11/197,197, filed Aug. 4, 2005, Office Action dated Jul. 6, 2007.
U.S. Appl. No. 11/197,197, filed Aug. 4, 2005, Office Action dated Apr. 12, 2007.
U.S. Appl. No. 11/197,197, filed Aug. 4, 2005, Office Action dated Sep. 27, 2006.
U.S. Appl. No. 11/210,345, filed Aug. 24, 2005, Office Action dated Sep. 28, 2009.
U.S. Appl. No. 11/210,345, filed Aug. 24, 2005, Office Action dated Jun. 23, 2009.
U.S. Appl. No. 11/210,345, filed Aug. 24, 2005, Office Action dated Jan. 9, 2009.
U.S. Appl. No. 11/210,345, filed Aug. 24, 2005, Office Action dated Sep. 10, 2008.
U.S. Appl. No. 11/210,345, filed Aug. 24, 2005, Office Action dated Apr. 8, 2008.
U.S. Appl. No. 11/210,345, filed Aug. 24, 2005, Office Action dated Oct. 18, 2007.
U.S. Appl. No. 11/210,345, filed Aug. 24, 2005, Office Action dated Feb. 12, 2007.
U.S. Appl. No. 11/224,462, filed Sep. 12, 2005, Office Action dated Oct. 23, 2009.
U.S. Appl. No. 11/224,462, filed Sep. 12, 2005, Office Action dated May 5, 2009.
U.S. Appl. No. 11/224,462, filed Sep. 12, 2005, Office Action dated Dec. 12, 2008.
U.S. Appl. No. 11/224,462, filed Sep. 12, 2005, Office Action dated May 28, 2008.
U.S. Appl. No. 11/224,462, filed Sep. 12, 2005, Office Action dated Nov. 29, 2007.
U.S. Appl. No. 11/224,462, filed Sep. 12, 2005, Office Action dated Jul. 10, 2007.
U.S. Appl. No. 11/231,511, filed Sep. 12, 2005, Office Action dated Sep. 28, 2009.
U.S. Appl. No. 11/231,511, filed Sep. 12, 2005, Office Action dated Jun. 19, 2009.
U.S. Appl. No. 11/231,511, filed Sep. 12, 2005, Office Action dated Dec. 30, 2008.
U.S. Appl. No. 11/231,511, filed Sep. 12, 2005, Office Action dated Sep. 23, 2008.
U.S. Appl. No. 11/231,511, filed Sep. 12, 2005, Office Action dated Mar. 4, 2008.
U.S. Appl. No. 11/231,511, filed Sep. 12, 2005, Office Action dated Aug. 22, 2007.
U.S. Appl. No. 11/231,511, filed Sep. 12, 2005, Office Action dated Jun. 7, 2006.
U.S. Appl. No. 11/231,512, filed Sep. 12, 2005, Office Action dated Jul. 22, 2009.
U.S. Appl. No. 11/231,512, filed Sep. 12, 2005, Office Action dated Jan. 6, 2009.
U.S. Appl. No. 11/231,512, filed Sep. 12, 2005, Office Action dated Jun. 27, 2008.
U.S. Appl. No. 11/231,500, filed Sep. 21, 2005, Office Action dated Sep. 28, 2009.
U.S. Appl. No. 11/231,500, filed Sep. 21, 2005, Office Action dated Jun. 24, 2009.
U.S. Appl. No. 11/231,500, filed Sep. 21, 2005, Office Action dated Jan. 8, 2009.
U.S. Appl. No. 11/231,500, filed Sep. 21, 2005, Office Action dated Sep. 22, 2008.
U.S. Appl. No. 11/231,500, filed Sep. 21, 2005, Office Action dated Mar. 4, 2008.
U.S. Appl. No. 11/231,500, filed Sep. 21, 2005, Office Action dated Aug. 22, 2007.
U.S. Appl. No. 11/231,500, filed Sep. 21, 2005, Office Action dated Jun. 8, 2006.
U.S. Appl. No. 11/232,193, filed Sep. 21, 2005, Notice of Allowance dated Aug. 28, 2007.
U.S. Appl. No. 11/232,193, filed Sep. 21, 2005, Office Action dated Jun. 7, 2006.
U.S. Appl. No. 11/286,614, filed Nov. 23, 2005, Office Action dated Nov. 20, 2009.
U.S. Appl. No. 11/286,614, filed Nov. 23, 2005, Office Action dated Jun. 8, 2009.
U.S. Appl. No. 11/286,614, filed Nov. 23, 2005, Office Action dated Jan. 2, 2009.
U.S. Appl. No. 11/286,614, filed Nov. 23, 2005, Office Action dated Jun. 11, 2008.
U.S. Appl. No. 11/709,500, filed Feb. 27, 2007, Office Action dated Aug. 28, 2009.
U.S. Appl. No. 11/709,500, filed Feb. 27, 2007, Office Action dated Sep. 25, 2008.
U.S. Appl. No. 11/713,906, filed Feb. 28, 2007, Office Action dated Sep. 15, 2009.
U.S. Appl. No. 11/713,906, filed Feb. 28, 2007, Office Action dated Apr. 13, 2009.
U.S. Appl. No. 11/713,906, filed Feb. 28, 2007, Office Action dated Jun. 26, 2008.

* cited by examiner

DISPOSABLE ABSORBENT ARTICLE HAVING DEPLOYABLE CHASSIS EARS

FIELD OF THE INVENTION

This invention relates to disposable absorbent articles such as disposable diapers and other articles intended for use on incontinent persons.

BACKGROUND OF THE INVENTION

Disposable absorbent articles are designed to absorb and contain bodily waste in order to prevent soiling of the body and clothing of the wearer, as well as bedding or other objects with which the wearer comes into contact.

As the usage of disposable absorbent articles has expanded, their complexity has increased with the incorporation of additional features serving to enhance their performance and appearance. The costs of the materials and the costs of the manufacturing processes have also increased in conjunction with the increase in complexity. As a result, the prices at which these articles are sold have risen to levels that many potential purchasers around the world cannot afford to pay. Thus, a need exists for a simple disposable absorbent article.

SUMMARY OF THE INVENTION

The present invention provides a simple disposable absorbent article including a chassis and an absorbent assembly. The chassis includes laterally opposing side flaps formed by laterally inwardly folded portions of the chassis and deployable chassis ears formed by other laterally inwardly folded portions of the chassis. Each chassis ear is held laterally inwardly folded until being deployed by being released and unfolded laterally outward so as to project laterally outward beyond the adjacent side flap. Fastening elements may be disposed on at least two of the chassis ears, the fastening elements being adapted for fastening the front waist region to the back waist region to encircle a waist and legs of a wearer. The absorbent assembly may be attached in a cruciform pattern to the chassis to allow portions of the chassis underlying the absorbent assembly and lying outside the cruciform attachment pattern to extend laterally.

BRIEF DESCRIPTION OF THE DRAWINGS

In the accompanying drawing figures, like reference numerals identify structurally corresponding elements, which may or may not be identical in the several exemplary embodiments that are depicted. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description.

In the drawing figures and in the written description, lowercase letters appended to reference numerals indicate generally symmetric elements, e.g., left and right symmetric elements may be respectively identified by the reference numerals 1a and 1b. A reference numeral without an appended lowercase letter identifies all of the elements to which that particular reference numeral applies, e.g., the same elements as a group may be designated 1.

DETAILED DESCRIPTION OF THE INVENTION

Figure 1:
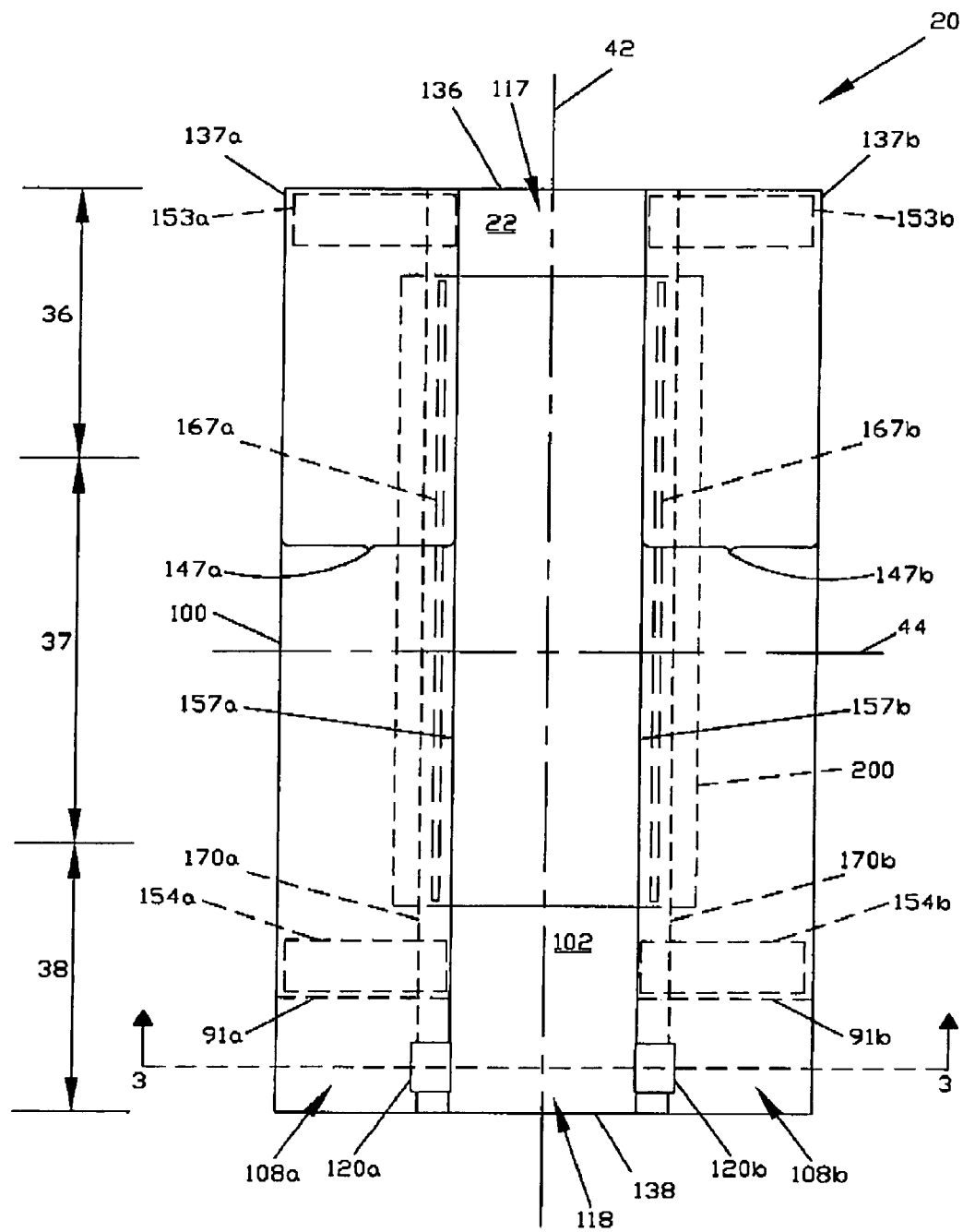
FIG. 1 is a plan view of an exemplary disposable absorbent article in the form of a diaper 20, which is shown in its flat, uncontracted state, i.e., without the contraction induced by elastic members. In this figure, the interior portion of the diaper 20 that faces inwardly toward the wearer and contacts the wearer is shown facing the viewer.

In this description, the following terms have the following meanings:

The term "absorbent article" refers to a device that absorbs and contains liquid, and more specifically, refers to a device that is placed against or in proximity to the body of a wearer to absorb and contain the various exudates discharged from the body.

The term "diaper" refers to an absorbent article that is generally worn by infants and incontinent persons about the lower torso so as to encircle the waist and the legs of the wearer and that is specifically adapted to receive and contain urinary and fecal waste.

The term "disposable" refers to the nature of absorbent articles that generally are not intended to be laundered or otherwise restored or reused as an absorbent article, i.e., they are intended to be discarded after a single use and, preferably, to be recycled, composted or otherwise disposed of in an environmentally compatible manner. In this description, a disposable diaper is described as being representative of an exemplary disposable absorbent article.

The term "deploy" in all its forms refers to the manipulation of any disclosed deployable structural element from its initial configuration to a configuration in which it can be used for its intended purpose in the article on which it is provided.

The term "longitudinal" refers to a direction running from a waist edge to an opposing waist edge of the article and generally parallel to the maximum linear dimension of the article.

The term "lateral" refers to a direction running from a side edge to an opposing side edge of the article and generally at a right angle to the longitudinal direction.

The term "diagonal" refers to an orientation of a line extending obliquely relative to the longitudinal and lateral directions, i.e., neither perpendicular nor parallel to either of the longitudinal or lateral directions.

The term "disposed" refers to an element being attached and positioned in a particular place or position in a unitary structure with other elements.

The term "attached" refers to elements being connected or united by fastening, adhering, bonding, etc. by any method suitable for the elements being attached together and their constituent materials. Many suitable methods for attaching elements together are well-known, including adhesive bonding, pressure bonding, thermal bonding, mechanical fastening, etc. Such attachment methods may be used to attach elements together over a particular area either continuously or intermittently.

The term "cohesive" refers to the property of a material that, once set, sticks to itself but does not to any significant degree stick to other materials.

The terms "water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water to pass through its thickness in the absence of a forcing pressure. Conversely, the term "water-impermeable" refers to a layer or a layered structure through the thickness of which liquid water cannot pass in the absence of a forcing pressure. A layer or a layered structure that is water-impermeable according to this definition may be permeable to water vapor, i.e., may be "water vapor-permeable". Such a water vapor-permeable layer or layered structure is commonly known in the art as "breathable". As is well known in the art, a common method for measuring the permeability to water of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "proximal" and "distal" refer respectively to the location of an element relatively near to or far from the center of a structure, e.g., the laterally proximal edge of a longitudinally extending element is located nearer to the longitudinal axis than the laterally distal edge of the same element is located relative to the same longitudinal axis. When used to describe relative locations with respect to the axes, synonyms include "inboard" and "outboard", respectively.

The terms "interior" and "exterior" refer respectively to the location of an element that is intended to be placed against or toward the body of a wearer when an absorbent article is worn and the location of an element that is intended to be placed against or toward any clothing that is worn over the absorbent article. Synonyms for "interior" and "exterior" include, respectively, "inner" and "outer", as well as "inside" and "outside". Also, when the absorbent article is oriented such that its interior faces upward, e.g., when it is laid out in preparation for setting the wearer on top of it, synonyms include "upper" and "lower", "above" and "below", "over" and "under", and "top" and "bottom", respectively.

As can be seen in the drawing figures, one end portion of the exemplary diaper 20 is configured as a front waist region 36, the longitudinally opposing end portion is configured as a back waist region 38, and an intermediate portion is configured as a crotch region 37.

The basic structure of the diaper 20 includes a chassis 100, which has a laterally extending front edge 136, a longitudinally opposing back edge 138, laterally opposing side edges 137, an interior surface 102, and an exterior surface 104. A longitudinal axis 42 extends through the midpoints of the front edge 136 and the back edge 138 and a lateral axis 44 extends through the midpoints of the side edges 137. The exemplary chassis 100 shown in FIG. 1 additionally has longitudinally extending and laterally opposing side flaps 147 as well as laterally opposing chassis ears 106 and/or 108, which are described in more detail below.

The basic structure of the diaper 20 also includes an absorbent assembly 200 that is attached to the chassis 100. The absorbent assembly 200 absorbs and retains liquid bodily waste materials. The absorbent assembly 200 has a laterally extending front edge 236, a longitudinally opposing back edge 238, laterally opposing side edges 237, an interior surface 202, and an exterior surface 204. The absorbent assembly 200 may be disposed either symmetrically or asymmetrically with respect to either or both of the longitudinal axis 42 and the lateral axis 44. For example, the absorbent assembly 200 shown in FIG. 1 is disposed symmetrically with respect to the longitudinal axis 42 and asymmetrically offset toward the front waist region 36 with respect to the lateral axis 44.

The edges of the absorbent assembly 200 may lie inward of the respective edges of the chassis 100, as in the exemplary diaper 20 shown in FIG. 1. Such a configuration in which one or more of the edges of the absorbent assembly 200 lies inward of the corresponding edges of the chassis 100 may be desirable, for example, in order to allow the relatively more flexible layer or layers adjacent to the edges of the chassis to conform to the body of the wearer and thereby form effective gasket-like seals against the skin of the wearer without being constrained by a relatively thicker and relatively less flexible absorbent assembly. Alternatively, one or more of the edges of the absorbent assembly 200 may coincide with the corresponding edge or edges of the chassis 100.

When the diaper 20 is worn on the lower torso of a wearer, the front waist edge 136 and the back waist edge 138 encircle the waist of the wearer, while at the same time the chassis side edges 137 encircle the legs of the wearer, the crotch region 37 is generally positioned between the legs of the wearer, and the absorbent assembly 200 extends from the front waist region 36 through the crotch region 37 to the back waist region 38.

Figure 15:
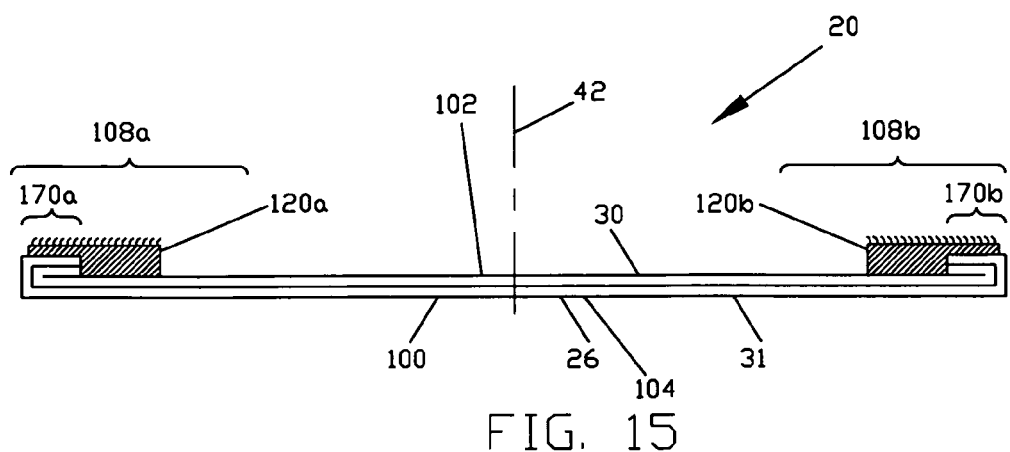
FIG. 15 is a section view of another exemplary diaper 20 taken at a section line similar to 13-13 and showing an alternative form of fasteners.
Figure 16:
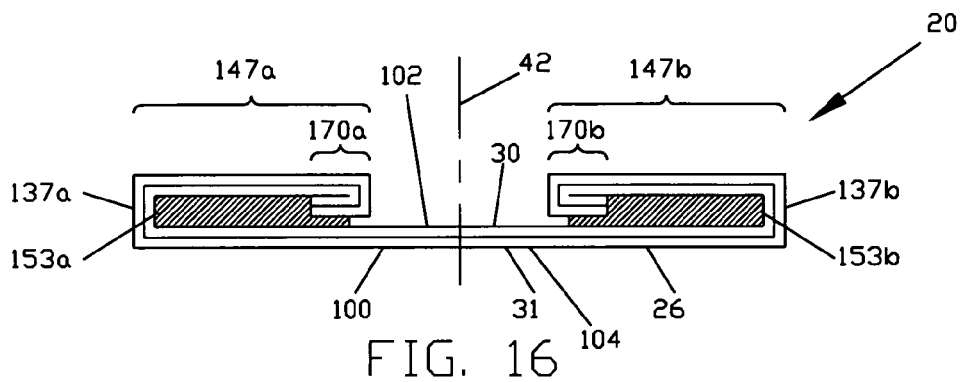
FIG. 16 is a section view of the diaper 20 of FIGS. 11 and 12 taken at the section line 16-16.

The chassis 100 includes a water-impermeable backsheet 26. The backsheet 26 forms an exterior surface that is intended to be placed toward any clothing that is worn over the diaper 20. Many suitable materials for use as the backsheet 26 are well-known, including films of polyethylene and other polyolefins. Multi-layer backsheets, such as laminates of a film and a nonwoven, are also well-known and may be suitable for use as the backsheet 26. Such a laminate backsheet may be oriented with the nonwoven 31 disposed exteriorly, as shown in FIG. 15 and FIG. 16, to provide the feel and appearance of a more cloth-like outermost layer than would be provided by using the film 30 as the outermost layer.

The chassis 100 may, but need not, additionally include an inner liner 22 attached to the backsheet 26. Such an inner liner 22 preferably is formed of a soft material that will not irritate the skin of the wearer. Many suitable materials for the inner liner 22 are well-known in the art, including rayon and synthetic nonwovens such as spunbonded or carded polypropylene or polyester. An inner liner 22 may form a portion of the interior surface 102 of the chassis 100 that is intended to be placed against the body of the wearer and thereby serve to isolate the skin of the wearer from a portion of the backsheet 26 as may be desirable, for example, when the diaper 20 is worn under conditions in which contact between the skin and a backsheet film could be uncomfortable.

The inner liner 22 may extend to the same width and the same length as the backsheet 26. For example, in the exemplary chassis 100 shown in FIG. 1 and FIG. 2, the edges of the inner liner 22 are not separately identified because the inner liner 22 has the same extent as the backsheet 26. Alternatively, one or more of the edges of the inner liner 22 may lie inward of the edges of the backsheet 26. For example, with reference to the exemplary diaper 20 shown in FIG. 1, only the portions of the inner liner 22 lying in the gap 117 between the front edge 236 of the absorbent assembly 200 and the front waist edge 136 of the chassis 100 and the gap 118 between the back edge 238 of the absorbent assembly 200 and the back waist edge 138 of the chassis 100 are exposed, while the remainder of the inner liner 22 is covered by the absorbent assembly 200 and the side flaps 147. Therefore, a laterally extending strip of the inner liner 22 disposed in the gap in the front waist region 36 and a similar laterally extending strip of the inner liner 22 disposed in the gap in the back waist region 38 may suffice to isolate the skin of the wearer from the backsheet 26 in these two gaps.

As shown in the figures, the exemplary chassis 100 has longitudinally extending and laterally opposing side flaps 147 that are disposed on the interior portion of the diaper 20 that faces inwardly toward the wearer and contacts the wearer. The side flaps 147 are formed by folding portions of the chassis 100 laterally inward, i.e., toward the longitudinal axis 42, to form both the respective side flaps 147 and the side edges 137 of the chassis 100, as shown in the figures Each side flap 147 has a proximal edge 157.

Figure 8:
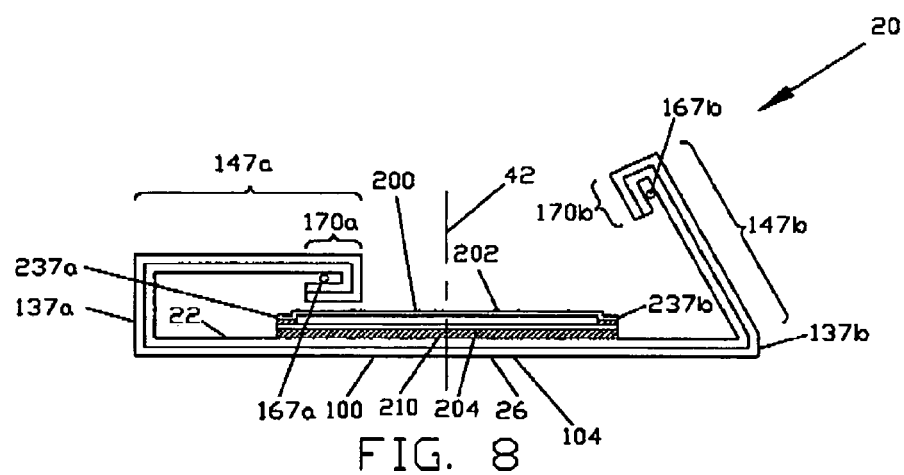
FIG. 8 is a section view of the diaper 20 of FIGS. 5 and 6 taken at the section line 8-8.
Figure 9:
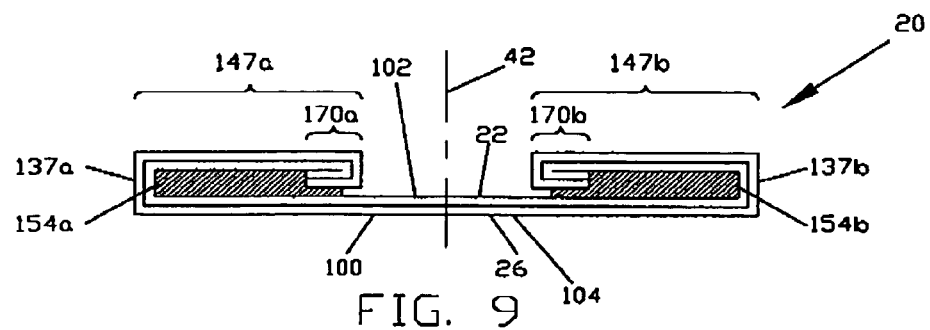
FIG. 9 is a section view of the diaper 20 of FIGS. 5 and 6 taken at the section line 9-9.
Figure 10:
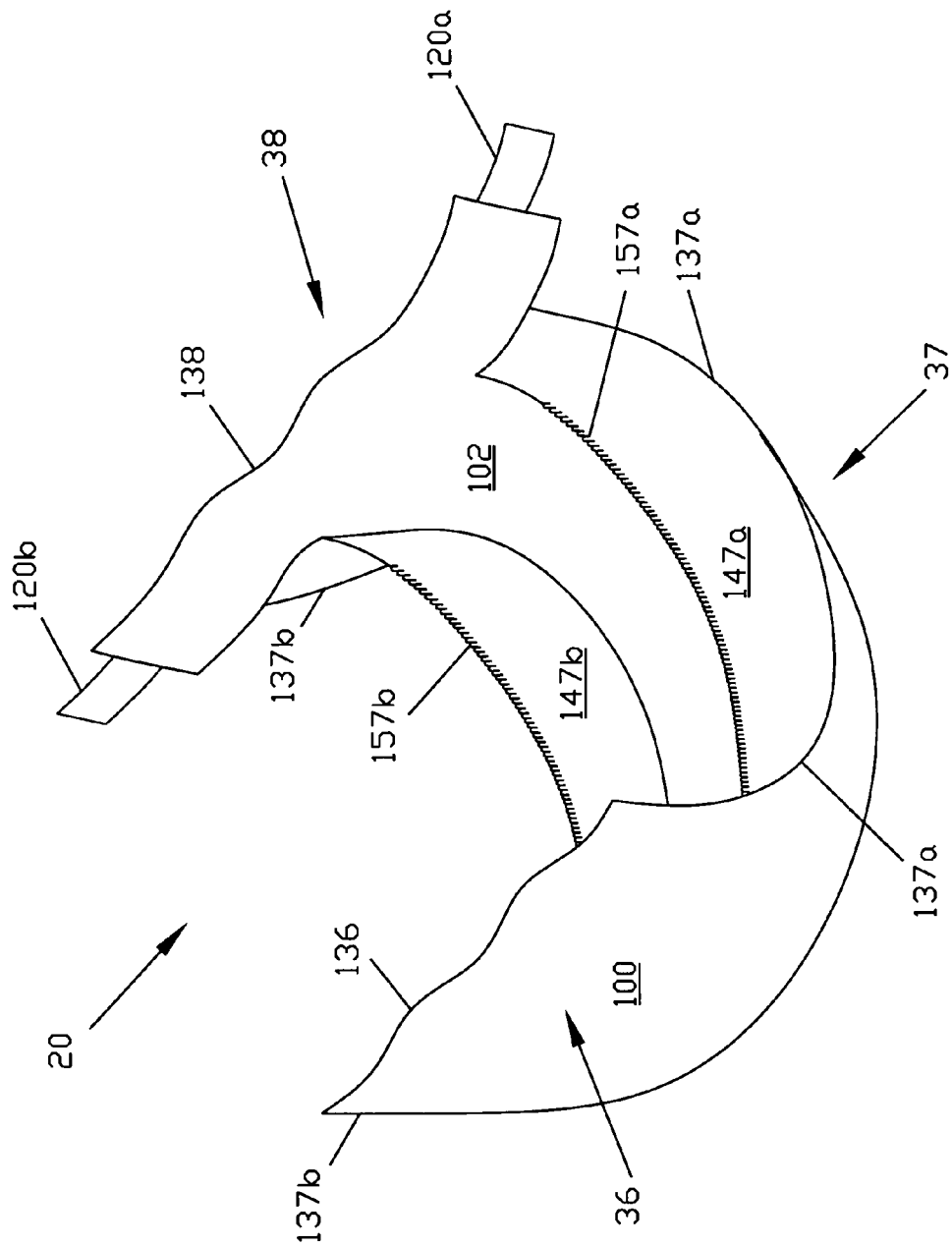
FIG. 10 is a perspective view of an exemplary diaper 20, which is shown in its relaxed, contracted state, i.e., with the contraction induced by elastic members. In this figure, the interior portion of the diaper 20 is shown facing upward.
Figure 11:
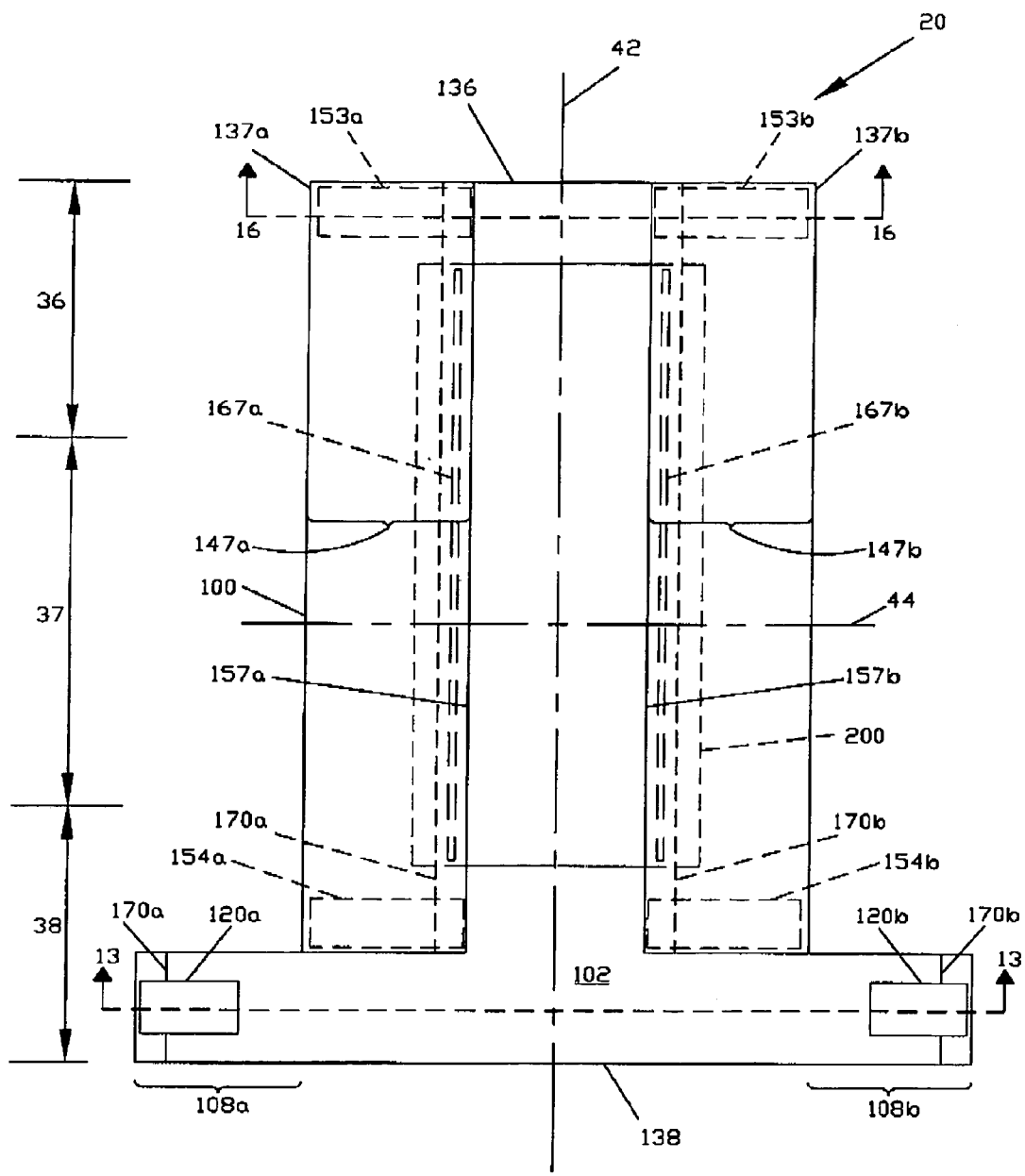
FIG. 11 is plan view of another exemplary diaper 20 showing an alternative form of fasteners.
Figure 12:
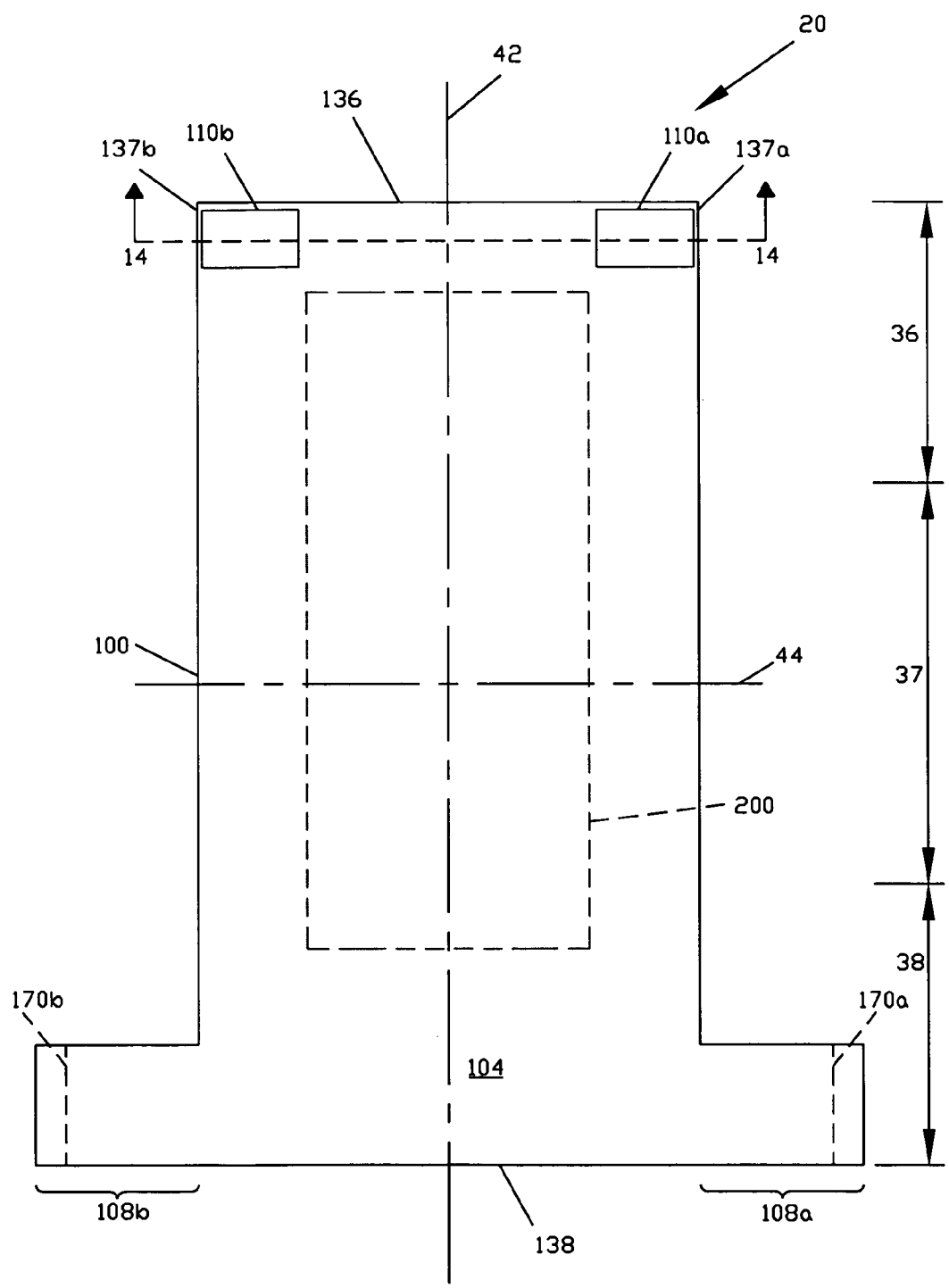
FIG. 12 is a plan view of the diaper 20 of FIG. 11 with the exterior portion of the diaper 20 shown facing the viewer.
Figure 13:
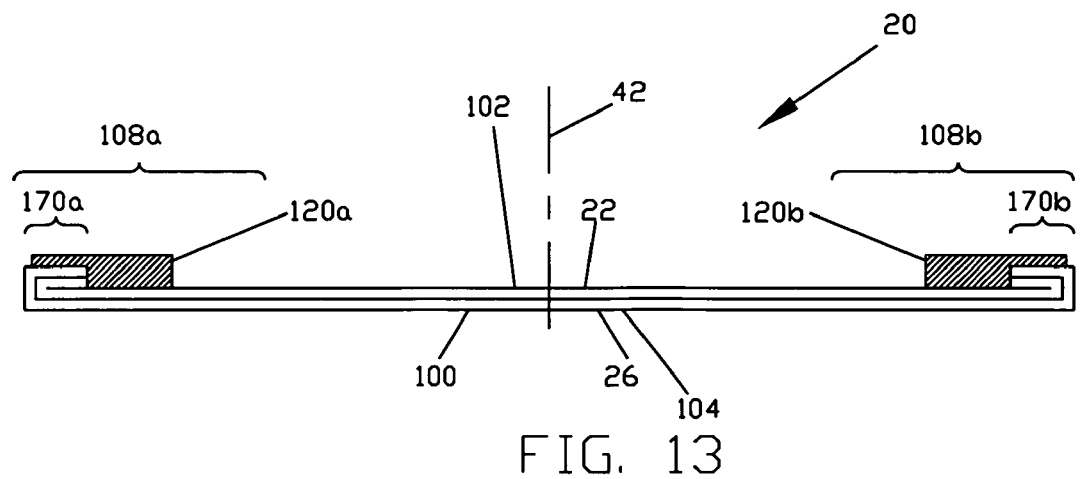
FIG. 13 is a section view of the diaper 20 of FIGS. 11 and 12 taken at the section line 13-13.
Figure 14:
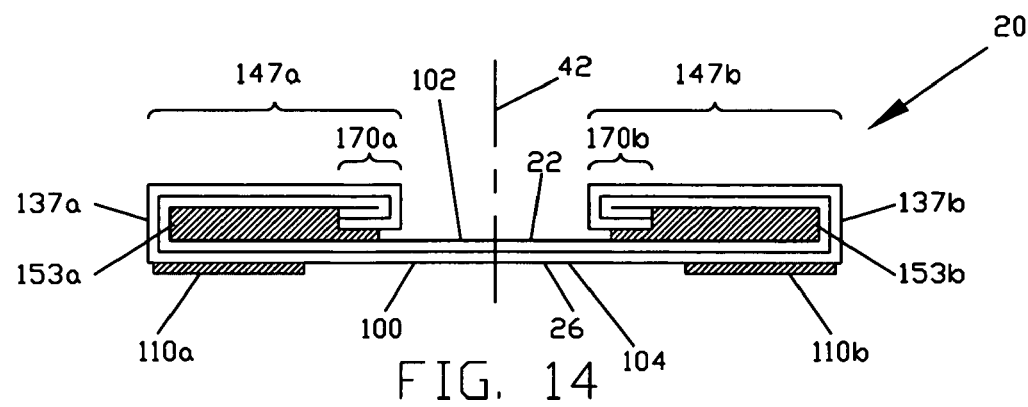
FIG. 14 is a section view of the diaper 20 of FIGS. 11 and 12 taken at the section line 14-14.

Each side flap 147 is attached to the interior surface 102 of the chassis 100 in attachment zone 153 adjacent to the front waist edge 136 and in a longitudinally opposing attachment zone 154 adjacent to the back waist edge 138, as shown in FIG. 9. Between the attachment zones, the proximal edge 157 of the side flap 147 remains free, i.e., not attached to the interior surface 102 of the chassis 100 or to the absorbent assembly 200. Also between the attachment zones, an elastic strand 167 is attached adjacent to the proximal edge 157 of each side flap 147. Each elastic strand 167 is enclosed inside a hem 170 formed adjacent to the proximal edge 157 of each side flap 147. When stretched, the elastic strand 167 allows the adjacent side flap edge to extend to the flat uncontracted length of the chassis. When allowed to relax, the elastic strands 167 contract and lifts the proximal edges 157, thereby lifting the side flaps 147 into position to serve as side barriers adjacent to the side edges 237 of the absorbent assembly 200, as shown in FIG. 8. This contraction gathers the adjacent side flap edges and thereby bends the diaper 20 into a "U" shape in which the interior of the "U" shape is formed by the portions of the diaper 20 that are intended to be placed toward the body of the wearer, as shown in FIG. 10.

When the diaper 20 is worn, the relaxed "U" shape generally conforms to the body of the wearer such that the front waist region 36 and the back waist region 38 can be fastened together to encircle the waist and the legs of the wearer. When the diaper 20 is worn in this manner, the elastic strands 167 tend to hold the lifted proximal edges 157 of the side flaps 147 in contact with the body of the wearer and thereby form seals to help prevent the leakage of deposited bodily waste out of the diaper 20. The lateral spacing of the lifted proximal edges 157 is selected to allow the deposit of bodily wastes from the lower torso of the wearer into the space between the lifted side flaps 147 and thereby directly onto the absorbent assembly 200. The width of each of the side flaps 147 in effect becomes its height when the free portion of its proximal edge is lifted and the side flap serves as a side barrier to leakage. This height preferably is selected to allow the lifted proximal edges 157 to fit into the leg creases of the body of the wearer at the same time as the absorbent assembly 200 is held in contact with the body.

Figure 5:
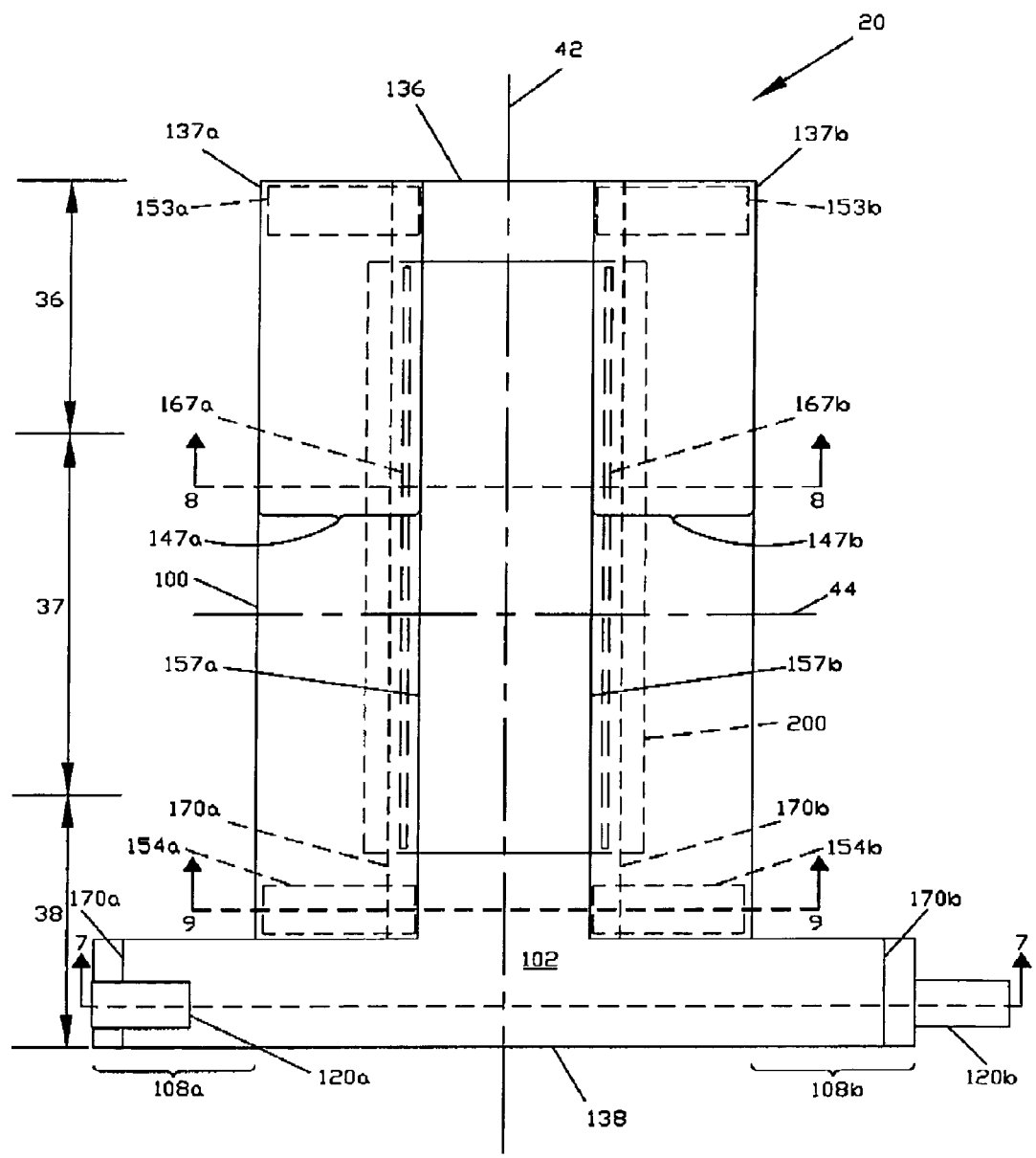
FIG. 5 is a plan view of the exemplary diaper 20 with two chassis ears extending laterally. In this figure, the interior portion of the diaper 20 is shown facing the viewer.
Figure 6:
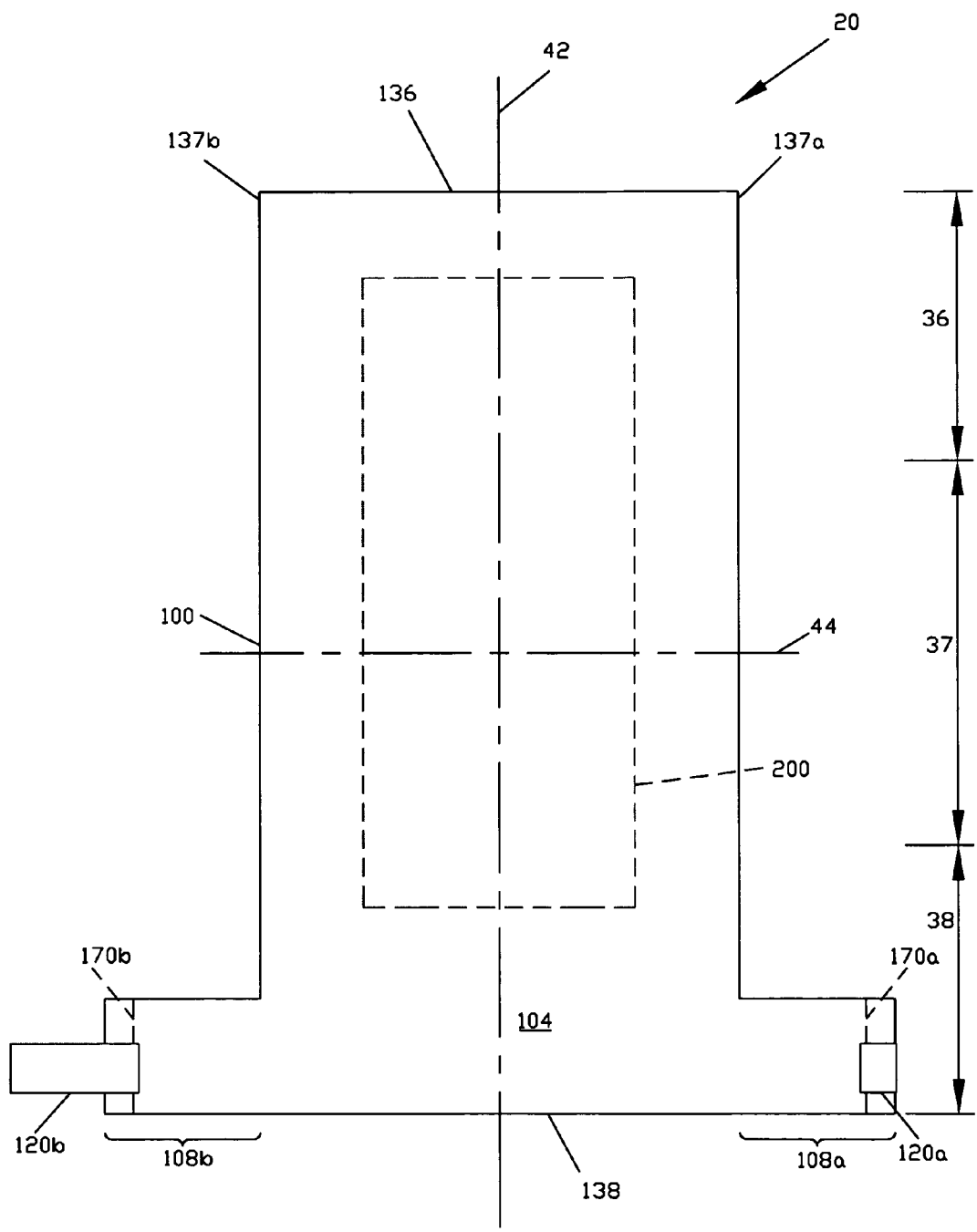
FIG. 6 is a plan view of the diaper 20 of FIG. 5 with the exterior portion of the diaper 20 shown facing the viewer.
Figure 24:
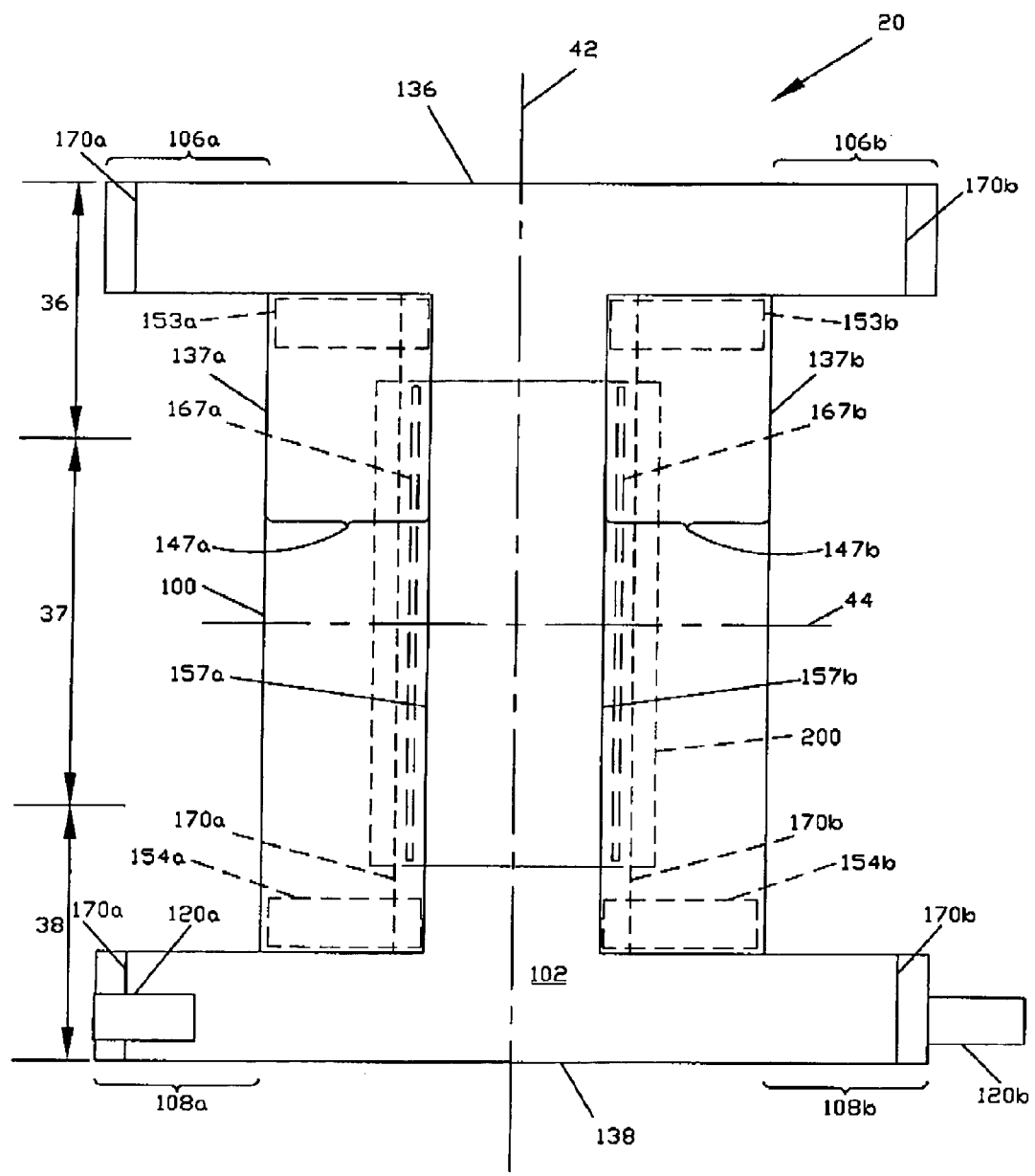
FIG. 24 is a plan view of another exemplary diaper 20 with four chassis ears extending laterally. In this figure, the interior portion of the diaper 20 is shown facing the viewer.

In the finished diaper, it is preferable that the chassis have side edges 137 that are not straight, but instead are notched, thereby giving an overall shape in plan view of a "T" or of an "I" to the diaper 20. Such a non-rectangular configuration may impart a tailored appearance to the diaper 20 when it is worn and may also impart an impression that the diaper 20 will fit comfortably between the legs of a wearer. An exemplary non-rectangular configuration of the chassis is shown in FIG. 5 and FIG. 6. As shown in these figures, laterally opposing portions 108 of the chassis 100 in the back waist region 138 may extend laterally outward while the adjacent side flaps 147 remain folded laterally inward. The laterally outwardly extending portions 108 form back chassis "ears" that impart a "T" shape to the diaper. Alternatively, laterally opposing portions 106 of the chassis 100 in the front waist region 136 may extend laterally outward to form front chassis ears and thereby impart a "T" shape to the diaper. As another alternative, both the front portions 106 and the back portions 108 may extend laterally outward to form four chassis ears while the adjacent side flaps 147 remain folded laterally inward, in which configuration an "I" shape is imparted to the diaper 20, as shown in FIG. 24.

For ease of manufacturing and packaging, it is preferable that the chassis ears 106 and/or 108 remain folded laterally inward until a user desires to deploy them for use when applying the diaper 20 onto the body of a wearer. For this purpose, as shown in FIG. 1, one edge of each chassis ear may be defined by a frangible line of attachment 91 along which the chassis ear can be partially detached for deployment, i.e., unfolding laterally outward. Such a frangible line of attachment may be formed in a layer or a laminate of layers by perforation, by the formation of a brittle area or areas at which the material will preferentially fracture when stressed, by the formation of a weaker area or areas at which the material will preferentially tear when stressed, by the formation of a friable area or areas at which the material will preferentially crumble when stressed and/or bent, or by any other method of providing frangibility that is suitable for the materials involved.

Figure 2:
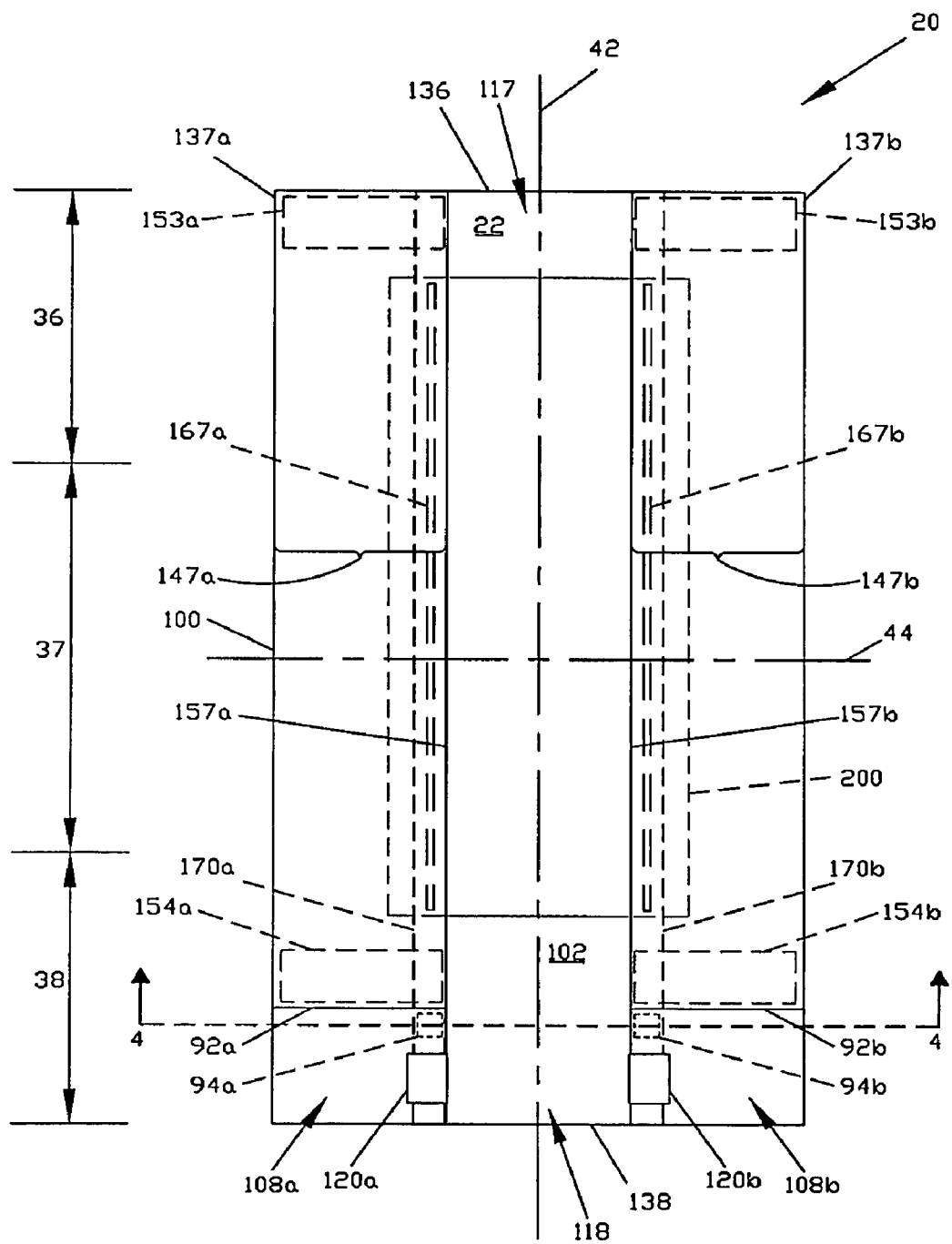
FIG. 2 is a plan view of an alternative embodiment of a diaper 20 with the interior portion of the diaper 20 that faces inwardly toward the wearer shown facing the viewer.
Figure 4:
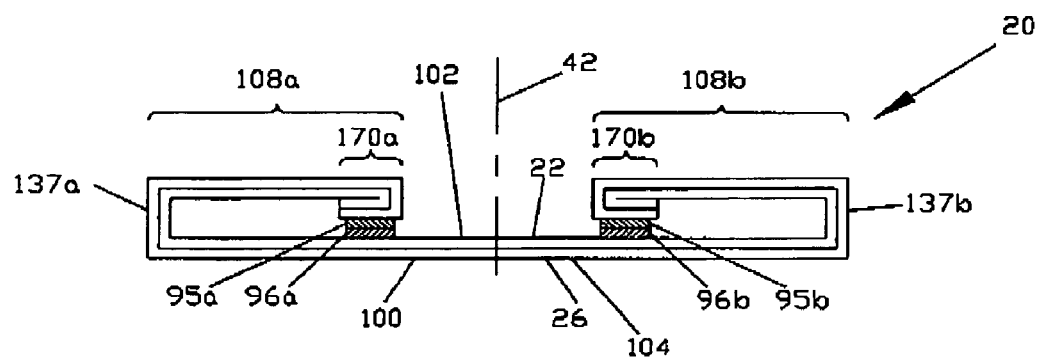
FIG. 4 is a section view of the diaper 20 of FIG. 2 taken at the section line 4-4.

Alternatively, as shown in FIG. 2, one edge of each chassis ear may be defined by a cut line 92 at which the chassis ear is severed from the adjacent side flap 147. Because the formation of this cut line would allow the chassis ear to unfold prematurely, the chassis ear may be held laterally inwardly folded by a releasable attachment member 94 until being deployed by being released and unfolded laterally outward so as to project laterally outward beyond the adjacent side flap. As shown in FIG. 4, the releasable attachment member 94 may include a releasable attachment element 95 disposed on the chassis ear and a complementary releasable attachment element 96 disposed on the interior surface 102 underlying the chassis ear when it is laterally inwardly folded. Such a releasable attachment member 94 may also be used in combination with a chassis ear that is defined by a frangible line of attachment 91 if additional assurance is desired that the chassis ear will not inadvertently be deployed prematurely, for example by handling that might rupture the frangible line of attachment.

The front waist region 36 and the back waist region 38 can be fastened together to encircle the waist and the legs of the wearer in many well-known ways. For example, separate fastening devices such as safety pins, separate tapes, a separate tie strap or straps, and/or a separate belt can be used for this purpose. Alternatively or in addition, fastening elements can be incorporated into the chassis 100 to enable a user to apply the diaper 20 to the body of the wearer without, or in conjunction with, any separate fastening devices. Many suitable types of such incorporated fastening elements are well-known, including, for example, tapes, adhesives, adhesive tape tabs, ties, buttons, hooks, loops, snap fasteners, other forms of mechanical fasteners, cohesive patches, etc. When configured for use, these incorporated fastening elements may project laterally or longitudinally outward or they may lie entirely inside the edges of the diaper 20.

For example, laterally opposing fastening elements may be attached to the chassis ears. The fastening elements 120 shown in the figures are disposed on the back chassis ears 108 and may be used to fasten the back waist region 38 to the front waist region 36 in a back-over-front manner. Alternatively, similar fastening elements may be disposed on front chassis ears 106 and used to fasten the front waist region 36 to the back waist region 38 in a front-over-back manner. As yet another alternative, similar fastening elements may be disposed on a waist region not having chassis ears extending from it and may be used to attach that waist region to chassis ears extending from the opposing waist region.

Figure 3:
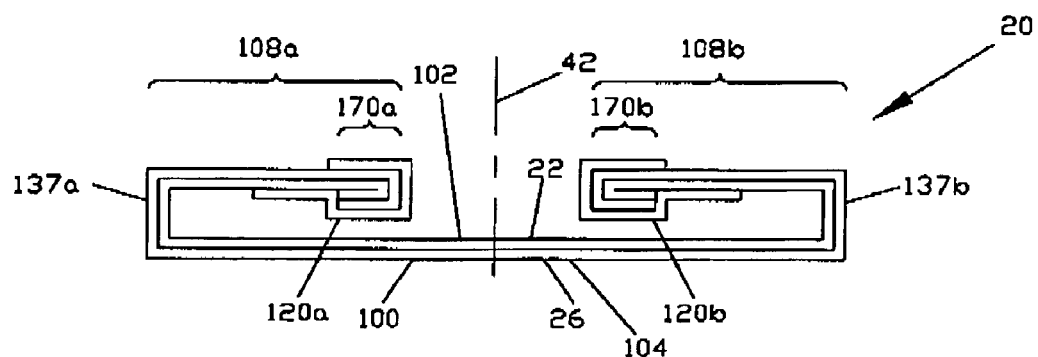
FIG. 3 is a section view of the diaper 20 of FIG. 1 taken at the section line 3-3.
Figure 7:
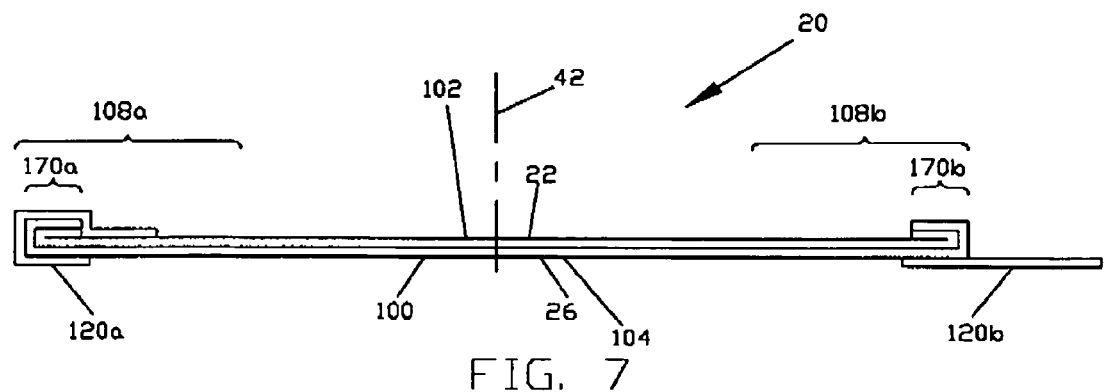
FIG. 7 is a section view of the diaper 20 of FIGS. 5 and 6 taken at the section line 7-7.

The fastening elements 120 shown in FIG. 5 and FIG. 6 project laterally outward from the chassis ears 108 in the form of tapes. Such tapes may be coated with an adhesive. Suitable adhesive tapes are available from the 3M Corporation of St. Paul, Minn., U.S.A., under the designation of XMF99121. In order to prevent their premature adhesion to a surface, such adhesive tape fastening elements are typically folded over to prevent exposure of the adhesive and subsequently unfolded to expose the adhesive for use. For example, in FIG. 3, both fastening elements 120 are shown folded, while in FIG. 5, FIG. 6, and FIG. 7, the left fastening element 120a is shown still folded and the right fastening element 120b is shown unfolded and thereby configured for use.

Optionally, a fastening sheet (not shown) may be attached onto the exterior surface 104 of the chassis 100, as described in U.S. Patent Application Publication No. 2005/0171499A1, published on 4 Aug. 2005. When a fastening sheet is provided, adhesive tape fastening elements may be adhered to the fastening sheet to fasten the back waist region 38 and the front waist region 36 together. The incorporation of such a fastening sheet may be desirable, for example, in order to make it possible to use a relatively inexpensive and relatively weak material for the backsheet 26.

Several configurations of cohesive fastening patches are described in U.S. Patent Application Publication No. 2005/0171499A1. In the present invention, it is preferable that such cohesive fastening patches be disposed on the chassis ears. For example, the back fastening elements 120 shown in FIG. 11, FIG. 12, FIG. 13, and FIG. 14, may be formed by cohesive fastening patches and the complementary front fastening elements 110 in the front waist region 36 may be formed by compatible cohesive fastening patches.

Alternatively, when a laminate backsheet is used and is oriented with the nonwoven disposed exteriorly, some forms of mechanical fasteners that typically require specific mating fastener elements, such as hooks that typically mate with loops, may be configured to engage with the nonwoven and thereby make the inclusion of the specific mating fastener element unnecessary. For example, as shown in FIG. 15, the fastening elements 120 may be formed by hook fastening patches configured to engage with the nonwoven layer 31 of the laminate backsheet 26. Such hook fastening elements may be disposed similarly to the cohesive fastening patch fastening elements shown in FIG. 13.

As described in U.S. Patent Application Publication No. 2005/0171499A1, a portion or the whole of the chassis 100 may be made extensible to a degree greater than the inherent extensibility of the material or materials from which the chassis is made, e.g., the backsheet 26, the inner liner 22, or both. The additional extensibility may be desirable in order to allow the chassis 100 to conform to the body of a wearer during movement by the wearer. The additional extensibility may also be desirable, for example, in order to allow the user of a diaper 20 including a chassis 100 having a particular size before extension to extend the front waist region 36, the back waist region 38, or both waist regions of the chassis 100 to encircle the waist of an individual wearer whose waist circumference falls within a predefined range, i.e., to tailor the diaper to the individual wearer. Such extension of the waist region or regions may give the diaper a generally hourglass shape, so long as the crotch region 37 is extended to a relatively lesser degree than the waist region or regions, and may impart a tailored appearance to the diaper 20 when it is worn. In addition, the additional extensibility may be desirable in order to minimize the cost of the diaper. For example, an amount of material that would otherwise be sufficient only to make a relatively smaller diaper lacking this extensibility can be used to make a diaper capable of being extended to fit a wearer larger than the smaller diaper would fit. In other words, a lesser amount of material is needed in order to make a diaper capable of being properly fitted onto a given size of a wearer when the material is made extensible as described.

Additional extensibility in the chassis 100 in the lateral direction is relatively more useful than additional extensibility in the longitudinal direction. The abdomen of the wearer is likely to expand when the wearer changes posture from standing to sitting and the corresponding abdominal expansion increases the circumference that is encircled by the waist edges of the chassis 100, necessitating the lateral extension of the waist region or regions.

Figure 17:
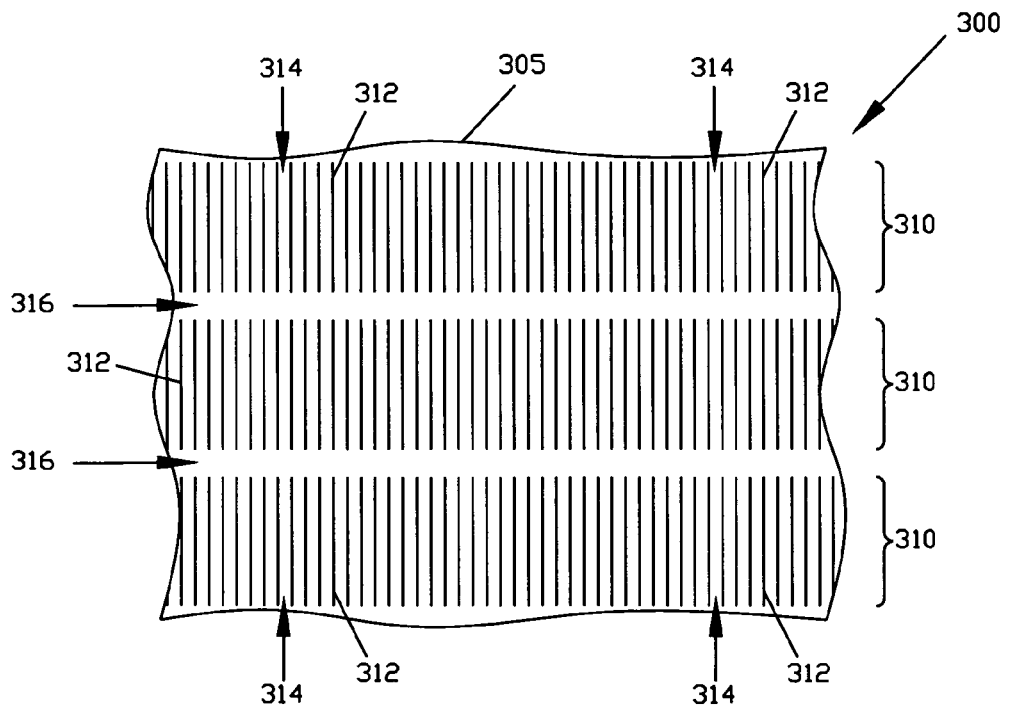
FIG. 17 is a plan view of an exemplary fragment of a formed web material.
Figure 18:
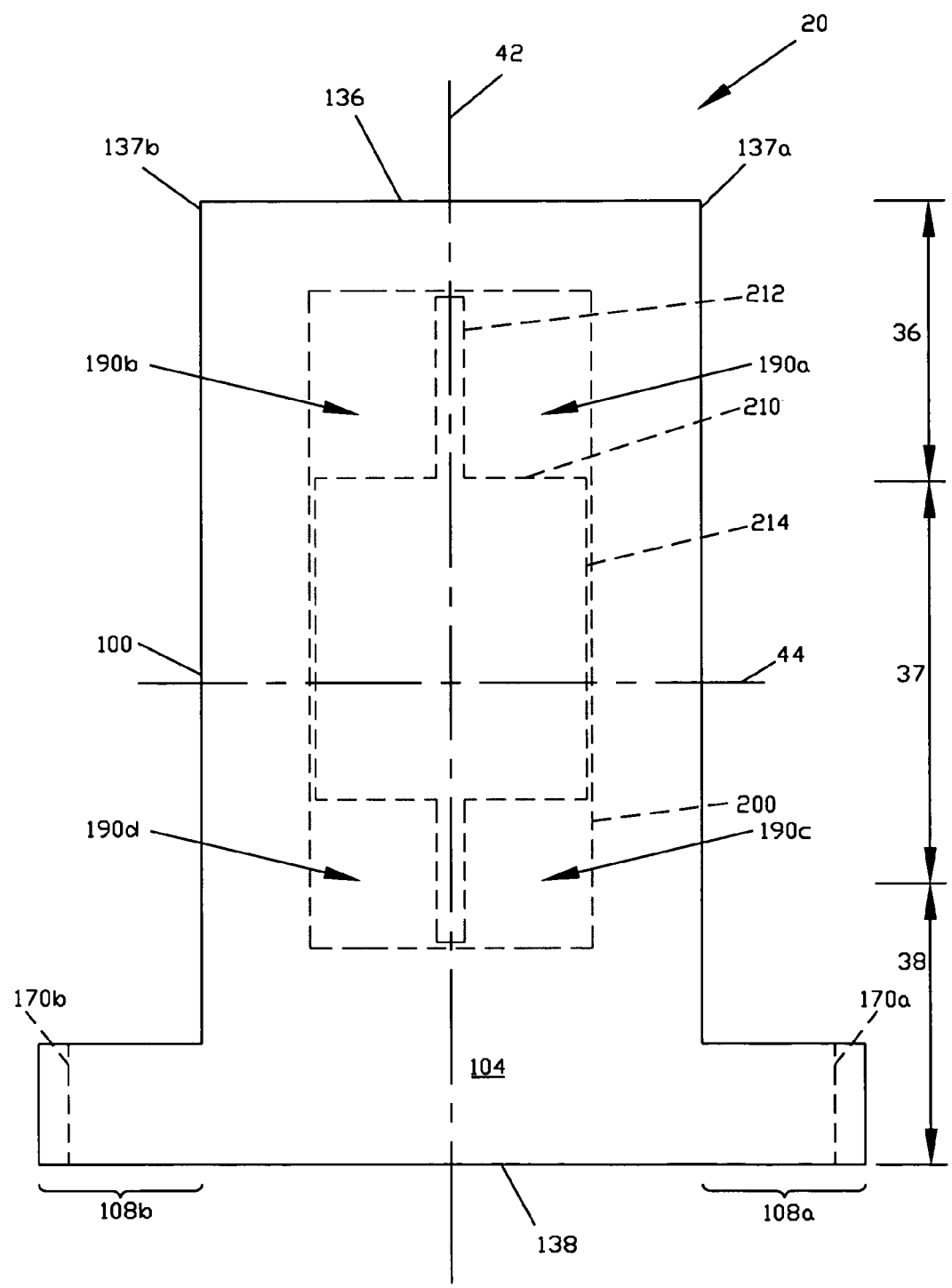
FIG. 18 is a simplified plan view of an exemplary diaper 20, which is shown in its flat, uncontracted state, i.e., without the contraction induced by elastic members, having the absorbent assembly attached to the chassis in a cruciform attachment pattern. In this figure, the exterior portion of the diaper 20 is shown facing the viewer.

Additional lateral extensibility in to chassis 100 may be provided in a variety of ways. For example, a material or materials from which the chassis 100 is made may be pleated by any of many known methods. Alternatively, all or a portion of the chassis may be made of a formed web material or a formed laminate of web materials like those described in U.S. Pat. No. 5,518,801 issued on 21 May 1996. An exemplary fragment 300 of such a formed web material 305 is shown in FIG. 17. This formed web material 305 includes distinct laterally extending regions 310 in which the original material has been altered by embossing or another method of deformation to create a pattern of generally longitudinally oriented alternating ridges 312 and valleys 314 in the web. The formed web material 305 also includes laterally extending unaltered regions 316 located between the laterally extending altered regions 310.

Such a formed web material 305 can be laterally extended beyond its original dimension with the application of relatively less force than that required to extend the same material to the same extent when undeformed. In particular, the effects of an application of opposing divergent forces directed generally perpendicular to the ridges 312 and valleys 314 include an extension of such a formed web material along an axis between the opposing forces and the generation of a resistive contractive force, primarily in the unaltered regions 316. This resistive force is relatively smaller than the resistive force that is generated by the same material in its unaltered form when extended to the same extent, at least up to an extension at which the ridges and valleys in the altered regions flatten and begin to contribute to the resistive force. Thus, such formed web materials exhibit an extensible behavior resembling that of traditional elastic materials in the range of extensibility that is useful for the type of lateral extension desired for use in absorbent articles. However, such formed web materials may be made of relatively less expensive materials that are not inherently elastic and, thus, their use may provide an advantage in terms of the cost of manufacturing the absorbent articles.

As shown in FIG. 19, FIG. 20, FIG. 21, and FIG. 22, the absorbent assembly 200 includes an absorbent core 250. The absorbent core 250 has a laterally extending front edge 256, a longitudinally opposing back edge 258, a left side edge 257a, and a laterally opposing right side edge 257b. Any or all of the edges of the absorbent core 250 may lie inward of, or may coincide with, the respective edges of the absorbent assembly 200. For example, in the exemplary absorbent assembly 200 shown in FIG. 19, the side edges 257 of the absorbent core 250 are located laterally inward of the side edges 237 of the absorbent assembly 200, while the front edge 256 and back edge 258 of the absorbent core 250 coincide with the respective front edge 236 and back edge 238 of the absorbent assembly 200.

The absorbent assembly 200 may be attached to the chassis 100 over any part or the whole of the area of the absorbent assembly 200. Preferably, the absorbent assembly 200 is attached on its exterior surface 204 to the chassis 100 in a cruciform attachment pattern, i.e., in an attachment pattern that forms or is arranged in a cross or "+" shape. The cruciform attachment pattern may be contiguous, i.e., all of its portions may be touching or connected throughout the pattern in an unbroken sequence. Alternatively, the cruciform attachment pattern may include detached portions and thereby lack contiguity but still be arranged such that the shape of the overall pattern is a cruciform. For example, a discontiguous cruciform attachment pattern may include a longitudinally extending portion disposed along the longitudinal axis and separate left and right laterally distal portions disposed along or adjacent to the lateral axis and thereby form a cruciform as the shape of the overall pattern. Within the extent of the cruciform attachment pattern 210, the absorbent assembly 200 may be attached to the chassis 100 continuously or intermittently. For example, a film of an adhesive may be applied continuously over the entire area of the cruciform attachment pattern and then used to continuously attach the absorbent assembly to the chassis. As an alternative example, an adhesive may be applied discontinuously at and inside the boundaries of the cruciform attachment pattern, such as in the form of dots, stripes, beads, spirals, etc., and then used to attach the absorbent assembly to the chassis.

An exemplary contiguous cruciform attachment pattern 210 is shown in FIG. 18, FIG. 19, FIG. 20, FIG. 21, and FIG. 22. The portions 190 of the chassis 100 that lie outside such a cruciform attachment pattern are not restrained by attachment to the absorbent assembly 200 and therefore remain extensible. In particular, a relatively narrow longitudinally extending portion 212 of a cruciform attachment pattern 210 like that shown in FIG. 18, FIG. 19, and FIG. 21 leaves the majority of the width of the chassis 100 in the front waist region 36 and in the back waist region 38 freely extensible and thereby allows extension of the chassis 100 in the lateral direction in these regions. A relatively wide laterally extending portion 214 of a cruciform attachment pattern 210 like that shown in FIG. 18, FIG. 19, FIG. 20, and FIG. 22 prevents the portion of the chassis 100 in the crotch region 37 to which the absorbent assembly 200 is attached from shifting relative to the absorbent assembly 200 in that region. A relatively wide laterally extending portion 214 of a cruciform attachment pattern 210 may also contribute to the effectiveness of the side flaps 147 when the elastic strands 167 lift the proximal edges 157 into contact with the body of the wearer. For example, if the chassis 100 in the crotch region 37 were free to shift laterally inward, i.e., toward the longitudinal axis 42 such that the left side edge 137a and/or the right side edge 137b moved toward the longitudinal axis 42, the side flaps 147 might easily distort and fail to maintain contact with the body. However, because the relatively wide laterally extending portion 214 of the cruciform attachment pattern 210 restrains the chassis 100 over a relatively wide portion of the width of the crotch region 37, the side flaps 147 are better supported at their bases while being lifted by the elastic strands 167

Figure 19:
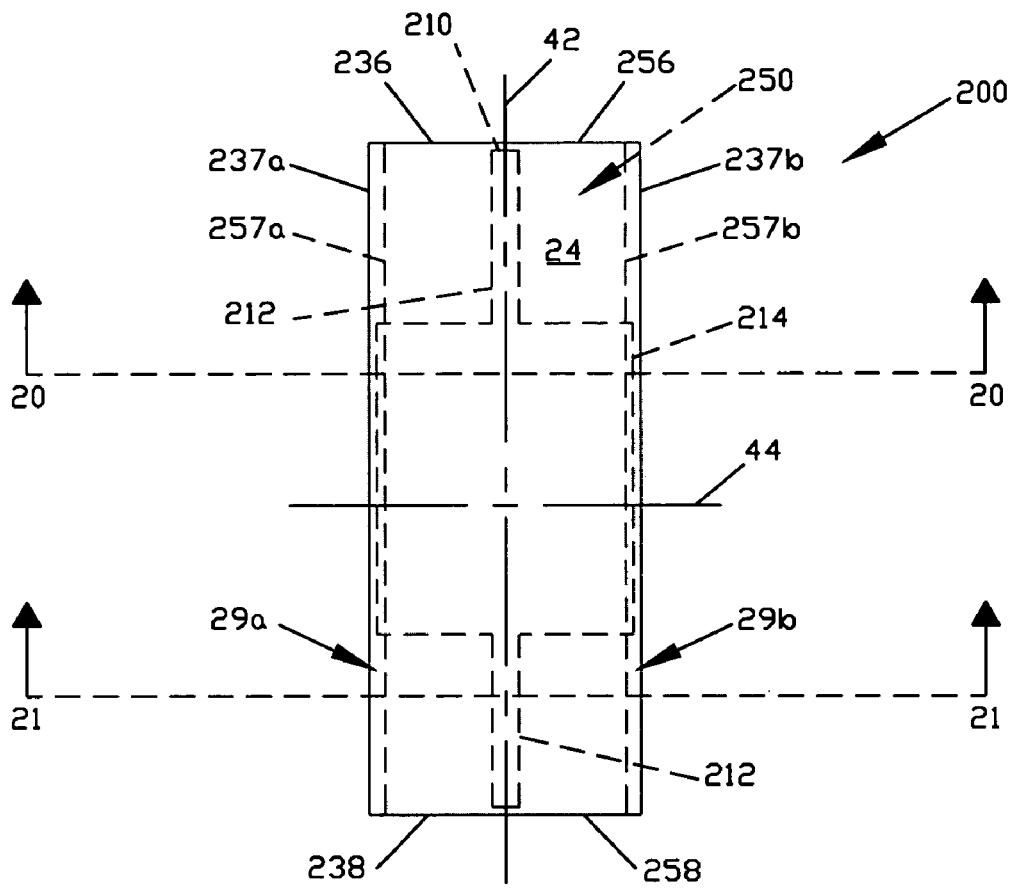
FIG. 19 is a plan view of an exemplary absorbent assembly 200. In this figure, the absorbent assembly 200 is shown separately from a chassis 100 to which it is attached in an exemplary diaper 20 and the interior portion of the absorbent assembly 200 that faces inwardly toward the wearer and contacts the wearer is shown facing the viewer.
Figure 20:
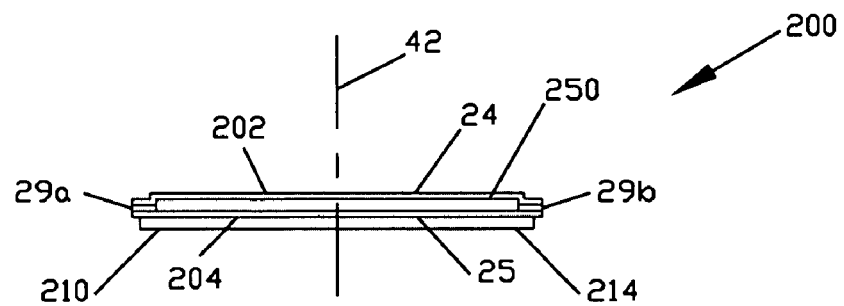
FIG. 20 is a section view of the absorbent assembly 200 of FIG. 19 taken at the section line 20-20.
Figure 21:
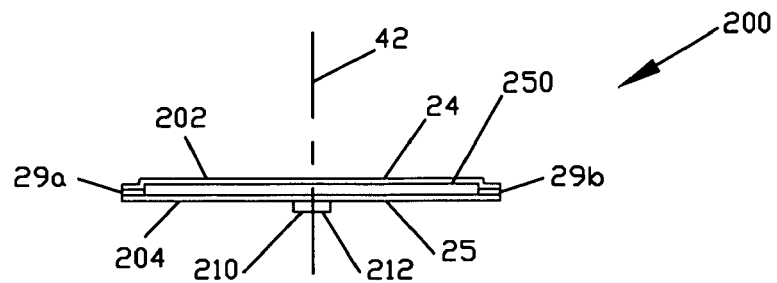
FIG. 21 is a section view of the absorbent assembly 200 of FIG. 19 taken at the section line 21-21.

The cruciform attachment pattern 210 may be disposed either symmetrically or asymmetrically with respect to either or both of the longitudinal axis 42 and the lateral axis 44 of the chassis 100. For example, the cruciform attachment pattern 210 shown in FIG. 19 is disposed symmetrically with respect to the longitudinal axis 42 and asymmetrically offset toward the front waist region 36 relative to the lateral axis 44.

The absorbent core 250 may be disposed between a lower covering sheet that is disposed on the exterior face of the absorbent core 250 in a face-to-face arrangement with the interior surface 102 of the chassis and an upper covering sheet that is disposed on the interior face of the absorbent core 250. Such an upper covering sheet and lower covering sheet may be attached together to contain the absorbent core 250 between them and thereby form the absorbent assembly 200. For example, in the exemplary absorbent assembly 200 shown in the figures, an upper covering sheet 24 and a lower covering sheet 25 are attached together at or adjacent to the side edges 237 of the absorbent assembly 200 in adhesive attachment zones 29. Alternatively, the upper covering sheet 24 and the lower covering sheet 25 may be attached together in places other than the side edges 237 of the absorbent assembly 200, e.g., at or adjacent to the end edges 236 and 238, or at or adjacent to both the end edges 236 and 238 and the side edges 237.

The upper covering sheet 24 is water-permeable and allows liquid waste to pass through to the absorbent core 250, where the liquid waste is absorbed. The lower covering sheet 25 may be water-impermeable. However, the lower covering sheet 25 preferably is water-permeable. In embodiments in which both the upper covering sheet 24 and the lower covering sheet 25 are water-permeable, any liquid waste that is deposited onto the upper covering sheet 24 but does not pass through the upper covering sheet 24 to the absorbent core 250 can flow around an edge of the absorbent assembly 200 to reach the lower covering sheet 25 and then pass through the lower covering sheet 25 to the absorbent core 250. The upper covering sheet 24 may form the interior surface 202 of the absorbent assembly 200 that is intended to be placed against the body of the wearer. The upper covering sheet 24 preferably is formed of a soft material that will not irritate the skin of the wearer. Many materials that are suitable for a water-permeable covering sheet are well-known in the art, including synthetic nonwovens such as spunbonded or carded polypropylene, polyester, or rayon. Likewise, many materials that are suitable for a covering sheet that is water-impermeable are well-known in the art, including the materials that are suitable for the backsheet 26.

Figure 22:
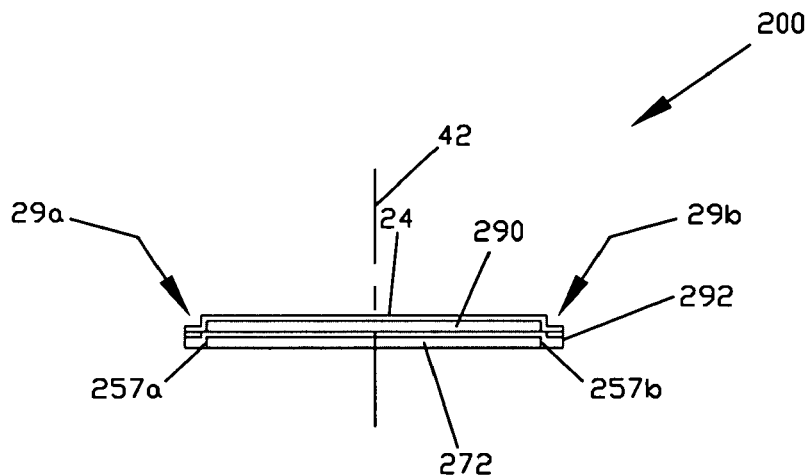
FIG. 22 is a section view of another exemplary absorbent assembly 200 taken at a section line similar to 20-20.

The absorbent core may include an acquisition component in addition to one or more storage components. The absorbent core acquisition component serves to acquire deposited liquid bodily waste material and transfer it to the absorbent core storage component. Any porous absorbent material which will imbibe and partition liquid bodily waste material to the storage component or components may be used to form the acquisition component. Preferred materials for the acquisition component include synthetic fiber materials, open celled polymeric foam materials, fibrous nonwoven materials, cellulosic nonwoven materials, and various combination synthetic/cellulosic nonwoven materials. Examples of such acquisition materials are more fully described in U.S. Pat. No. 4,950,264 issued on Aug. 21, 1990. High loft nonwoven acquisition materials suitable for the acquisition component of the present invention can be obtained from Polymer Group, Inc., (PGI), 450 N.E. Blvd, Landisville, N.J. 08326, U.S.A., under the material code designation of 98920. Such an absorbent core 250 including an acquisition component 290 overlying an absorbent core storage component 272 is shown in FIG. 22. A separation sheet 292 of, e.g., a tissue or a nonwoven material, may be disposed between the absorbent core storage component 272 and the absorbent core acquisition component 290 to help ensure that none of the gel formed by a superabsorbent polymer that may be included in the absorbent core storage component reaches the skin of the wearer.

Suitable well-known absorbent materials for the absorbent core include cellulose fibers in the form of comminuted wood pulp, which is commonly known as "airfelt", layers or sheets of natural or synthetic fibrous material, superabsorbent polymer, etc. These absorbent materials may be used separately or in combination and many may be used in a discrete form, i.e., in the form of fibers, granules, particles, layers and the like.

Figure 23:
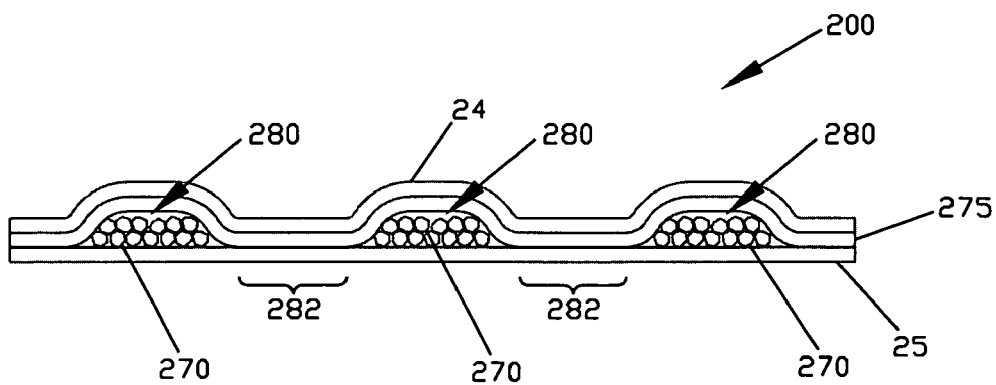
FIG. 23 is a section view of an exemplary absorbent core 250.

The discrete form of an absorbent material may be immobilized in pockets formed by a layer of a thermoplastic material, such as a hot melt adhesive, that intermittently contacts and adheres to a substrate, such as a covering sheet, while diverging away from the substrate at the pockets. Absorbent assemblies having such pocket structures are described in detail in U.S. Patent Application Publications Nos. 2004/0167486 of 26 Aug. 2004 and 2004/0162536 of 19 Aug. 2004. An exemplary absorbent assembly 200 having such a structure is shown in FIG. 23. In this absorbent assembly 200, the absorbent core 250 includes particles of superabsorbent polymer 270 that are contained inside pockets 280 formed by a layer 275 of a thermoplastic material. This absorbent core 250 contains no cellulose fibers. Alternatively, the absorbent core 250 may include both particles of superabsorbent polymer and airfelt and both materials may be contained inside the pockets. As shown in FIG. 23, the layer 275 of the thermoplastic material intermittently contacts and adheres to the lower covering sheet 25 at the areas of attachment 282. Between the areas of attachment 282, the layer 275 diverges away from the lower covering sheet 25 to form the pockets 280. The layer 275 may have the form of a sheet of fibers of the thermoplastic material through which the liquid waste may pass to the particles of superabsorbent polymer 270 to be absorbed. In FIG. 23, a separate upper covering sheet 24 is shown overlying the layer 275 of the thermoplastic material. Alternatively, the separate upper covering sheet 24 may be omitted and the layer 275 in the form of a fibrous sheet may serve as the upper covering sheet 24.

The disclosures of all patents, patent applications and any patents which issue thereon, as well as any corresponding published foreign patent applications, and all publications listed and/or referenced in this description, are hereby incorporated in their entireties herein by reference. It is expressly not admitted that any of the documents or any combination of the documents incorporated herein by reference teaches or discloses the present invention. In the case of any conflict between the definitions of terms, the usage in this description overrides the conflicting usage in any incorporated reference.

What is claimed is:

1. A disposable diaper comprising:

a chassis having a front waist region, a back waist region, and a crotch region between the waist regions, a longitudinal axis and a lateral axis, laterally opposing side edges, longitudinally opposing front and back waist end edges, an interior surface and an exterior surface;

the chassis including a water-impermeable backsheet;

the chassis also including laterally opposing side flaps formed by laterally inwardly folded portions of the chassis in at least the crotch region, each side flap having longitudinally distal ends and a proximal edge, each side flap being attached to the interior surface adjacent to the longitudinally distal ends and having a longitudinally extending elastic gathering member attached adjacent to the proximal edge;

the chassis also including laterally opposing deployable chassis ears formed by portions of the side flaps in at least one of the waist regions, each chassis ear being held laterally inwardly folded by a frangible line of attachment until being deployed by being detached at the frangible line and each side flap portion, in its entirety, being unfolded laterally outward so as to form the chassis ears projecting laterally outward beyond the respective side flap;

an absorbent assembly attached to the interior surface of the chassis;

wherein the absorbent assembly is attached to the chassis in a cruciform pattern of attachment having a longitudinally extending portion intersecting a laterally extending portion;

wherein a portion of the chassis underlying the absorbent assembly and lying outside the cruciform pattern is laterally extensible; and wherein the extensible portion of the chassis comprises a formed web material including at least two distinct laterally extending embossed regions each containing a pattern of generally longitudinally oriented alternating ridges and valleys created by an embossment and also containing an unembossed region located between the embossed regions, such that the portion of the chassis can be laterally extended to a given extent with the application of relatively less force than that required to laterally extend the same portion of the chassis to the same given extent before the embossment.

2. The disposable diaper of claim 1 wherein the chassis includes the chassis ears in both of the waist regions.

3. The disposable diaper of claim 1 wherein the chassis includes fastening elements disposed on at least two of the chassis ears and adapted for fastening the front waist region to the back waist region to encircle a waist and legs of a wearer.

4. The disposable diaper of claim 3 wherein the fastening elements comprise adhesive tapes.

5. The disposable diaper of claim 1 wherein the chassis includes a nonwoven inner liner attached to the backsheet and forming a portion of the interior surface.

6. The disposable diaper of claim 1 wherein the backsheet is a laminate of a film and a nonwoven, the nonwoven being disposed exteriorly of the film.

7. The disposable diaper of claim 6 wherein the fastening elements comprise hooks adapted to engage with the backsheet nonwoven.

8. The disposable diaper of claim 1 wherein the longitudinally extending portion is disposed symmetrically with respect to the longitudinal axis and the laterally extending portion is disposed asymmetrically with respect to the lateral axis.

9. The disposable diaper of claim 8 wherein the laterally extending portion is longitudinally offset toward the front waist region.

10. The disposable diaper of claim 1 wherein the frangible line of attachment comprises perforations.

11. A disposable diaper comprising:

a chassis having a front waist region, a back waist region, and a crotch region between the waist regions, a longitudinal axis and a lateral axis, laterally opposing side edges, longitudinally opposing front and back waist end edges, an interior surface and an exterior surface;

the chassis comprising a water-impermeable backsheet;

comprising laterally opposing side flaps formed by laterally inwardly folded portions of the backsheet in at least the crotch region, each side flap comprising longitudinally distal ends and a proximal edge;

the backsheet also comprising laterally opposing deployable first and second ears formed by portions of the side flaps in at least one of the waist regions, fastening elements being disposed on the first and second ears and adapted for fastening the front waist region to the back waist region to encircle a waist and legs of a wearer, the first and second ears being held laterally inwardly folded by a releasable attachment member until being deployed by being released at the attachment member and each side flap portion, in its entirety, being unfolded laterally outward so as to form the chassis ears projecting laterally outward beyond the respective side flap;

an absorbent assembly attached to the interior surface of the chassis;

wherein the absorbent assembly is attached to the chassis in a cruciform pattern of attachment having a longitudinally extending portion intersecting a laterally extending portion;

wherein a portion of the chassis underlying the absorbent assembly and lying outside the cruciform pattern is laterally extensible; and wherein the extensible portion of the chassis comprises a formed web material including at least two distinct laterally extending embossed regions each containing a pattern of generally longitudinally oriented alternating ridges and valleys created by an embossment and also containing an unembossed region located between the embossed regions, such that the portion of the chassis can be laterally extended to a given extent with the application of relatively less force than that required to laterally extend the same portion of the chassis to the same given extent before the embossment.

12. The disposable diaper of claim 11 wherein the releasable attachment member comprises an adhesive.

13. The disposable diaper of claim 11 wherein the releasable attachment member comprises complementary releasable attachment elements disposed on the first and second ears and on the interior surface underlying the laterally inwardly folded first and second ears.

14. The disposable diaper of claim 11 wherein the absorbent assembly comprises a plurality of discrete pockets of absorbent material.

15. A disposable diaper comprising:

a chassis having a front waist region, a back waist region, and a crotch region between the waist regions, a longitudinal axis and a lateral axis, laterally opposing side edges, longitudinally opposing front and back waist end edges, an interior surface and an exterior surface;

the chassis including a water-impermeable backsheet and a nonwoven inner liner attached to the backsheet and forming a portion of the interior surface;

the chassis also including laterally opposing side flaps formed by laterally inwardly folded portions of the chassis in at least the crotch region, each side flap having longitudinally distal ends and a proximal edge, each side flap being attached to the interior surface adjacent to the longitudinally distal ends and having a longitudinally extending elastic gathering member attached adjacent to the proximal edges;

the chassis also including laterally opposing deployable chassis ears formed by portions of the side flaps in each of the waist regions, fastening elements being disposed on at least two of the chassis ears, the fastening elements comprising adhesive tapes and being adapted for fastening the front waist region to the back waist region to encircle a waist and legs of a wearer, each chassis ear being held laterally inwardly folded by a frangible line of attachment until being deployed by being detached at the frangible line and each side flap portion, in its entirety, being unfolded laterally outward so as to form the chassis ears projecting laterally outward beyond the respective side flap;

an absorbent assembly attached to the interior surface of the chassis;

wherein the absorbent assembly is attached to the chassis in a cruciform pattern of attachment having a longitudinally extending portion intersecting a laterally extending portion;

wherein a portion of the chassis underlying the absorbent assembly and lying outside the cruciform pattern is laterally extensible; and wherein the extensible portion of the chassis comprises a formed web material including at least two distinct laterally extending embossed regions each containing a pattern of generally longitudinally oriented alternating ridges and valleys created by an embossment and also containing an unembossed region located between the embossed regions, such that the portion of the chassis can be laterally extended to a given extent with the application of relatively less force than that required to laterally extend the same portion of the chassis to the same given extent before the embossment.

* * * * *

UNITED STATES PATENT AND TRADEMARK OFFICE
CERTIFICATE OF CORRECTION

| | | |
|---|---|---|
| PATENT NO. | : 7,737,324 B2 | Page 1 of 1 |
| APPLICATION NO. | : 11/286934 | |
| DATED | : June 15, 2010 | |
| INVENTOR(S) | : Gary Dean LaVon et al. | |

It is certified that error appears in the above-identified patent and that said Letters Patent is hereby corrected as shown below:

Cover Page
(74) *Attorney, Agent, or Firm,* delete "Richad" and insert -- Richard --.
Column 9
Line 4, delete "to" and insert -- the --.

Signed and Sealed this
Fourteenth Day of June, 2011

David J. Kappos
*Director of the United States Patent and Trademark Office*